(12) United States Patent
Schmaus et al.

(10) Patent No.: US 8,911,795 B2
(45) Date of Patent: *Dec. 16, 2014

(54) COMPOSITIONS COMPRISING DIHYDROAVENANTHRAMIDE D AND CLIMBAZOLE AS COSMETIC AND PHARMACEUTICAL COMPOSITIONS FOR ALLEVIATING ITCHING

(75) Inventors: Gerhard Schmaus, Höxter (DE); Joachim Röding, Badenweiler (DE)

(73) Assignee: Symrise AG, Holzminden (DE)

( * ) Notice: Subject to any disclaimer, the term of this patent is extended or adjusted under 35 U.S.C. 154(b) by 1390 days.

This patent is subject to a terminal disclaimer.

(21) Appl. No.: 12/095,453

(22) PCT Filed: Nov. 3, 2006

(86) PCT No.: PCT/EP2006/068077
§ 371 (c)(1),
(2), (4) Date: Apr. 23, 2009

(87) PCT Pub. No.: WO2007/062957
PCT Pub. Date: Jun. 7, 2007

(65) Prior Publication Data
US 2009/0226537 A1  Sep. 10, 2009

Related U.S. Application Data

(60) Provisional application No. 60/740,690, filed on Nov. 30, 2005.

(51) Int. Cl.
| | | |
|---|---|---|
| A01N 59/16 | (2006.01) |
| A61K 33/32 | (2006.01) |
| A61Q 5/00 | (2006.01) |
| A61K 31/196 | (2006.01) |
| A61K 8/44 | (2006.01) |
| A61Q 19/00 | (2006.01) |

(52) U.S. Cl.
CPC ............ *A61Q 5/006* (2013.01); *A61K 2800/75* (2013.01); *A61K 31/196* (2013.01); *A61K 8/445* (2013.01); *A61Q 19/00* (2013.01)
USPC ............ 424/640; 514/188; 514/345; 514/563

(58) Field of Classification Search
None
See application file for complete search history.

(56) References Cited

U.S. PATENT DOCUMENTS

| | | | |
|---|---|---|---|
| 4,070,484 A | 1/1978 | Harita et al. | |
| 8,409,552 B2 * | 4/2013 | Schmaus et al. | ................. 424/61 |
| 2003/0161802 A1 * | 8/2003 | Flammer et al. | ............. 424/70.1 |
| 2003/0228272 A1 | 12/2003 | Amjad et al. | |
| 2006/0089413 A1 * | 4/2006 | Schmaus et al. | .............. 514/563 |

FOREIGN PATENT DOCUMENTS

| | | | | |
|---|---|---|---|---|
| JP | 2005187398 | 7/2005 | | |
| WO | WO-2004035015 | 4/2004 | | |
| WO | WO 2004/047833 | * 6/2004 | .......... A61K 31/196 |
| WO | WO-2004047833 | 6/2004 | | |
| WO | WO-2006134013 | 12/2006 | | |
| WO | WO-2006134120 | 12/2006 | | |

OTHER PUBLICATIONS

Wilbrand, G., "Dealing with Dandruff," Soap Perfumery and Cosmetics, United Trade Press Ltd. London, GB, vol. 72, No. 4, 1999, pp. 79-83, XP009082627, ISSN: 0037-749X, Abstract.
Wilbrand G., "Vergleichsstudie Ichthyol Pale Versus Zink Pyrithion (Bei Kopfschuppen, Juckreiz, Fettigem Haar)," Kosmetische Medizin, Grosse Verlag GMBH, Berlin, DE, vol. 20, No. 5, Nov. 1999, pp. 252-253, XP009082589, ISSN: 1430-4031, Abstract.

* cited by examiner

*Primary Examiner* — Carlos Azpuru
*Assistant Examiner* — David Browe
(74) *Attorney, Agent, or Firm* — Dilworth & Barrese, LLP

(57) ABSTRACT

Compositions comprising dihydroavenanthramide D and climbazole; and, cosmetics or pharmaceutical end products comprising the compositions, useful for treating skin and/or hair.

13 Claims, No Drawings

COMPOSITIONS COMPRISING DIHYDROAVENANTHRAMIDE D AND CLIMBAZOLE AS COSMETIC AND PHARMACEUTICAL COMPOSITIONS FOR ALLEVIATING ITCHING

CROSS REFERENCE TO RELATED APPLICATIONS

The application claims the benefit of PCT/EP2006/068077 filed on Nov. 3, 2006, and of U.S. Provisional Patent Application 60/740,690 filed on Nov. 30, 2005, the disclosures of which are hereby incorporated by reference.

BACKGROUND OF THE INVENTION

The present invention relates to mixtures of anthranilic acid amides and antidandruff agents which can be used especially as cosmetic and pharmaceutical compositions for alleviating itching.

WO 2004/047833, on which the present invention is based, discloses that certain anthranilic acid amides (of Formula 1) inhibit the substance P-induced release of histamines from mast cells and thus are suitable as cosmetic and pharmaceutical compositions for alleviating itching. The compounds of Formula 1 indicated in WO 2004/047833 are also particularly preferred for use within the framework of the present invention.

WO 2004/047833 discloses that the use concentration of a particular compound of Formula 1 is up to 10 percent by weight, based on the total weight of a ready-to-use cosmetic or pharmaceutical end product. In some cases, however, such high use concentrations seem to be problematic for cosmetic and/or pharmaceutical reasons relating e.g. to formulation technology.

BRIEF SUMMARY OF THE INVENTION

The object of the present invention was therefore to provide mixtures active in the alleviation of itching and/or the reduction of skin reddening which contain, in addition to one or more compounds of Formula 1:

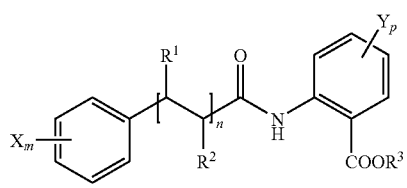

(see below for definitions of substituents and variables), another compound which interacts synergistically with the compound(s) of Formula 1 so that even low use concentrations of the compound(s) of Formula 1 and the other compound are sufficient to produce a good effect in the alleviation of itching or the reduction of reddening.

This object is achieved according to the invention by the provision of a mixture comprising or consisting of:
(a) one or more compounds of Formula 1:

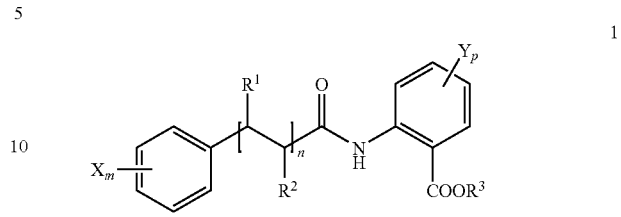

where the symbols in the compound or each compound of Formula 1 are defined as follows:
m=0, 1, 2 or 3,
p=0, 1 or 2,
n=0, 1 or 2,
where, when n=1 or 2, $R^1$ and $R^2$ in pairs are each H or together are another chemical bond (e.g. in cinnamic acid derivatives),
where, when m=1, 2 or 3, each X independently of the others is OH, Oalkyl or Oacyl,
and where, when p=1 or 2, each Y independently of the others is OH, Oalkyl or Oacyl,
and
$R^3$=H or alkyl (especially $CH_3$, linear or branched alkyl chains having 2 to 30 C atoms), $R^3$=H also representing the corresponding cosmetically or pharmaceutically acceptable salts and solvates;
and
(b) one or more antidandruff agents.

DETAILED DESCRIPTION OF THE INVENTION

Formula 1 above thus covers all the compounds of Formula 1 from WO 2004/047833 as well as some compounds not covered by the disclosure of WO 2004/047833.

Although it is already known from WO 2004/047833 that a cosmetic preparation can contain, in addition to a compound of Formula 1 (with the somewhat narrower definition according to WO 2004/047833), other active compounds for alleviating reddening and itching, WO 2004/047833 does not disclose that the addition of antidandruff agents leads to a synergistic intensification of the action of a compound of Formula 1 (with the somewhat broader definition according to the present invention).

Although it is known that certain antidandruff agents can reduce susceptibility to itching and thereby exert an alleviating effect (G. Wilbrand, Kosmetische Medizin Vol. 20(5), pp 252-253, 1999), there are no disclosures relating to the combination of antidandruff agents with compounds of Formula 1. Likewise, there are no disclosures relating to the synergistic interaction of antidandruff agents with compounds of Formula 1.

Particularly preferred compounds of Formula 1 for use in the mixture according to the invention are those in which:
n=1 or 2 and the sum p+m>0
and/or
p+m>0 and X or Y is selected at least once from the group comprising OH and Oacyl.

It is particularly preferable to use a compound of Formula 1 in which:
n=1
and
p+m≥2,
with the proviso that X and Y together are selected at least twice from the group comprising OH and Oacyl.

It is also preferable to use a compound of Formula 1 in which:

n=1, and also:

m=1, 2 or 3, with the proviso that X is selected at least once from the group comprising OH and Oacyl, and/or p=1 or 2, with the proviso that Y is selected at least once from the group comprising OH and Oacyl.

If n has the value 1, $R^1$ and $R^2$ are each preferably H, although it is also possible for $R^1$ and $R^2$ together to be another chemical bond.

The compound of Formula 1 is preferably selected from the group comprising:

2

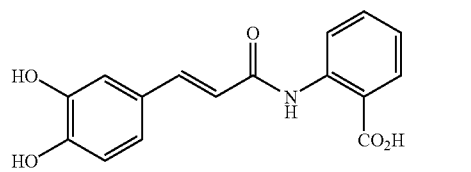

3

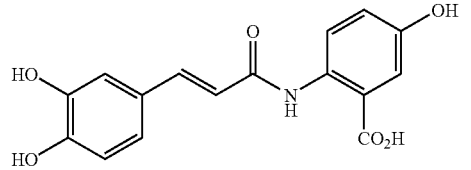

4

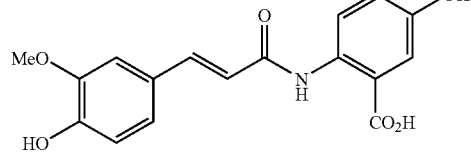

5

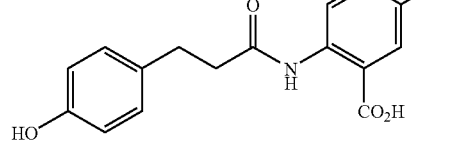

6

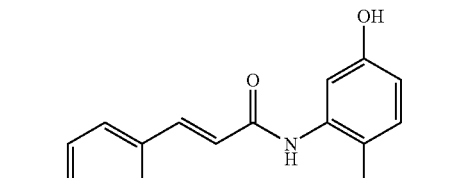

7

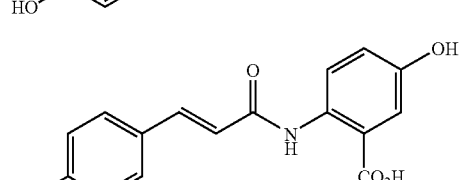

8

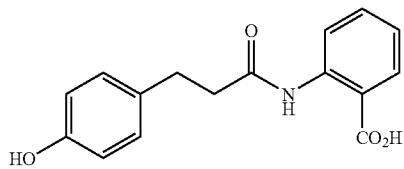

9

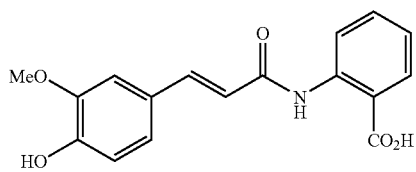

10

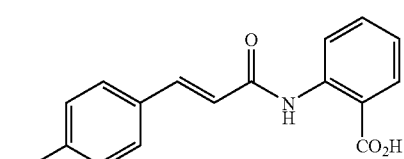

11

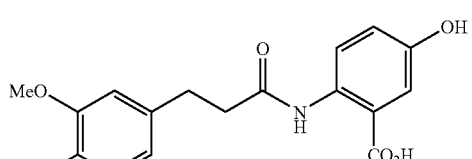

12

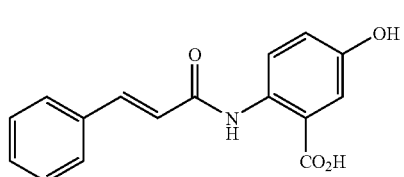

13

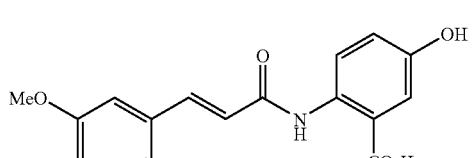

30

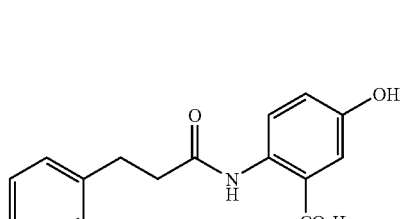

31

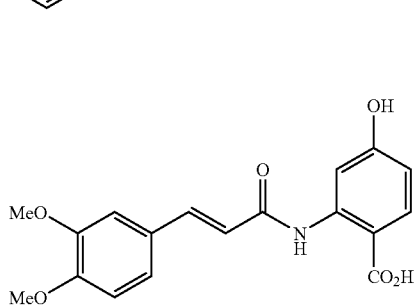

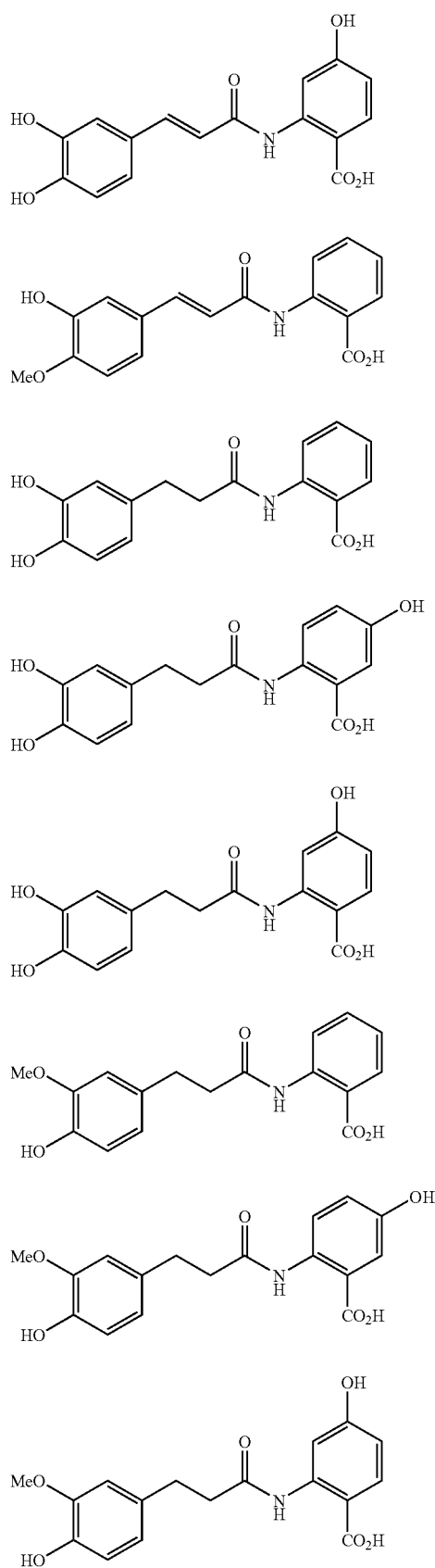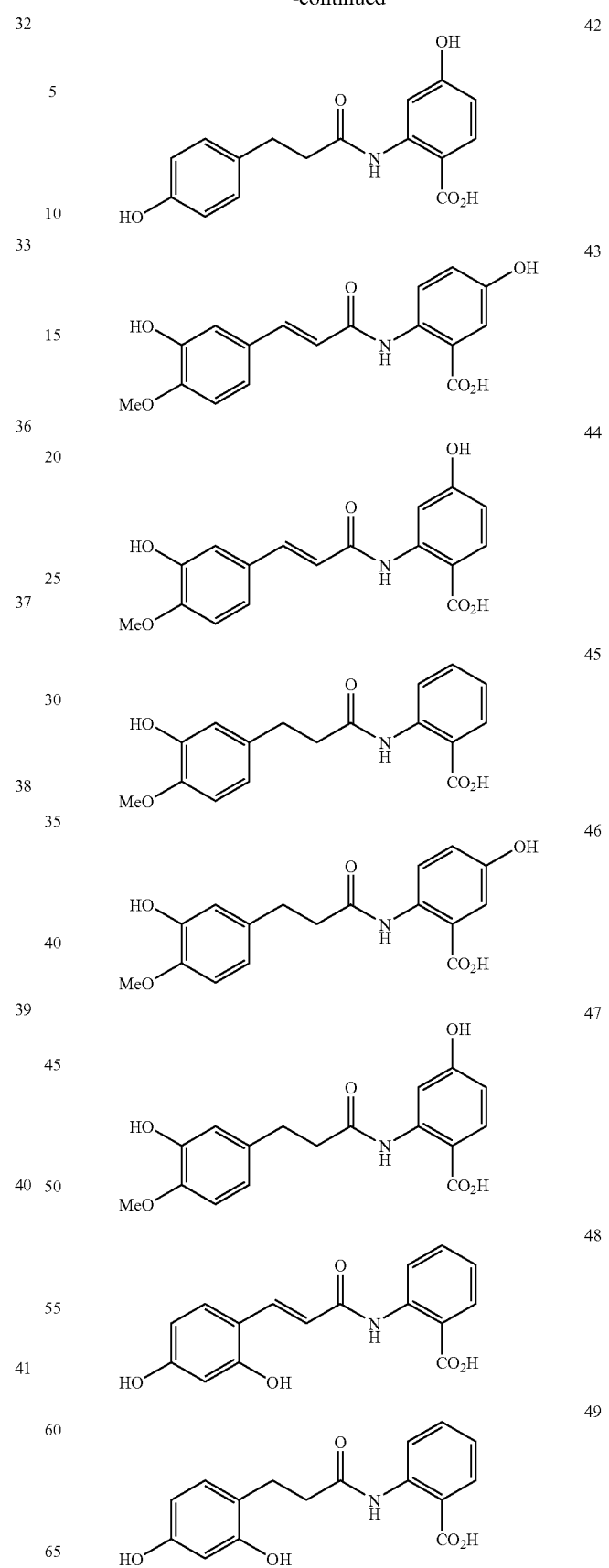

50
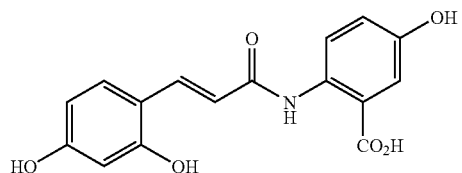
51
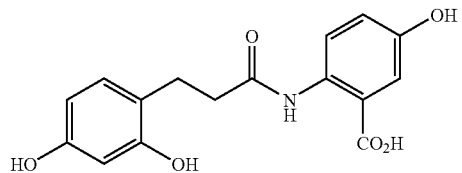
52
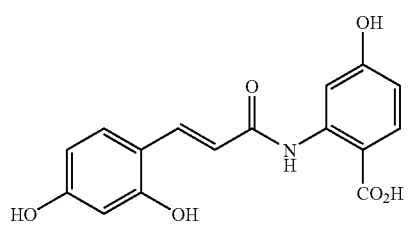
53
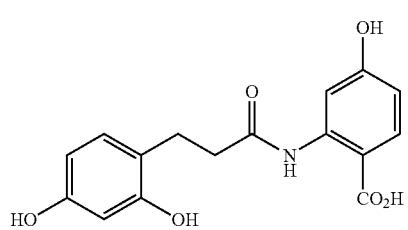
54
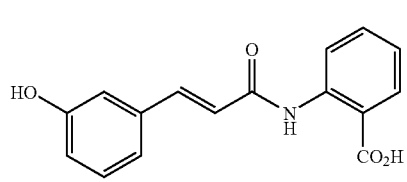
55
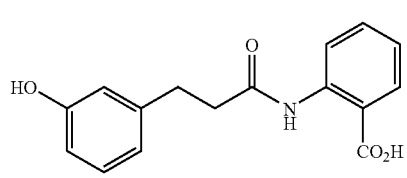
56
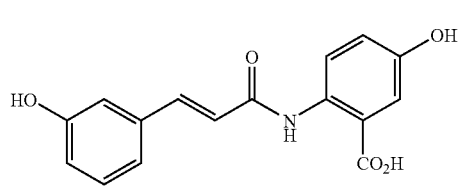
57
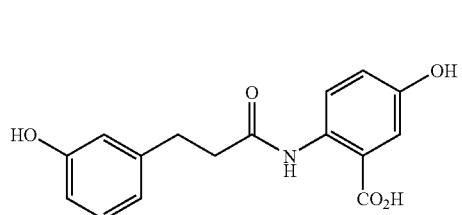
58
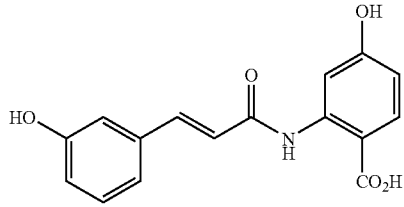
59
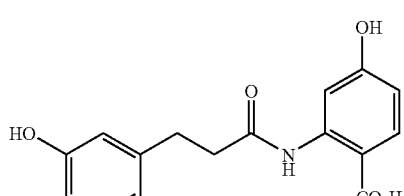
60
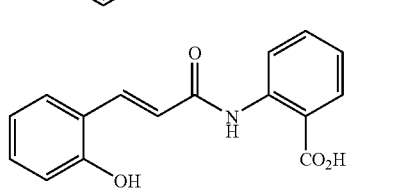
61
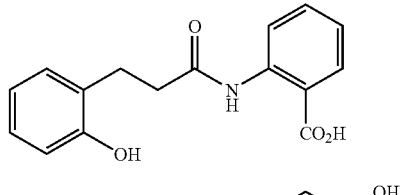
62
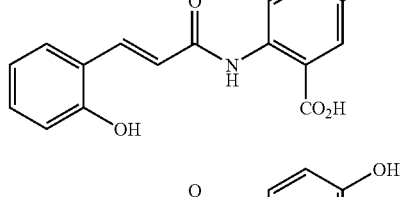
63
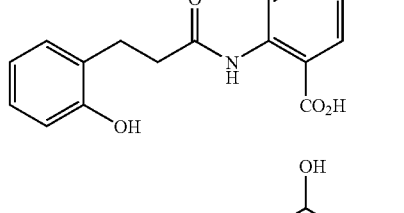
64
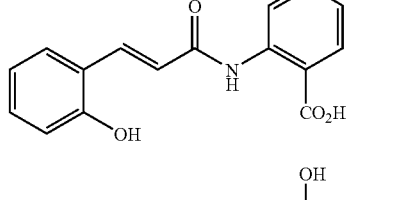
65
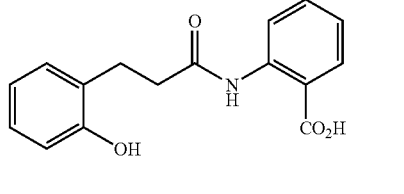
The above illustrations relate essentially to compounds of Formula 1 in which n=1.

However, the use of compounds of Formula 1 in which n=0 is also frequently preferred, in which case the following definition preferably applies:

m+p≥2, with the proviso that at least two of the substituents X and Y are selected from the group comprising OH and Oacyl.

It is particularly preferable to use compounds of Formula 1 (where n=0) selected from the group comprising:

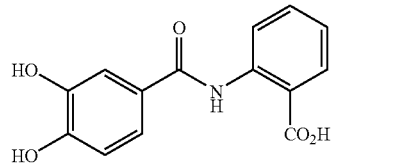

20

21

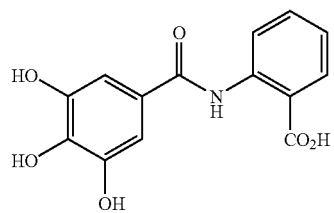

22

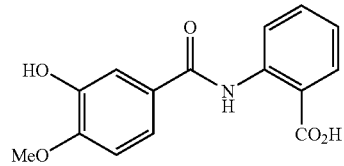

23

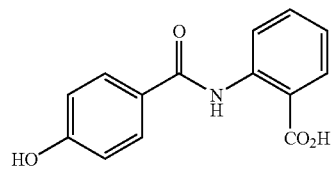

24

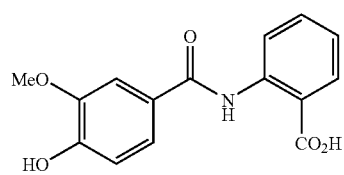

25

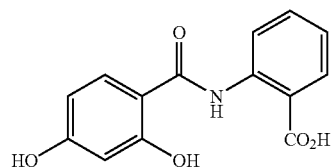

26

27

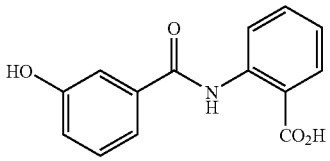

28

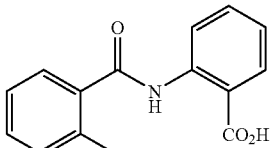

29

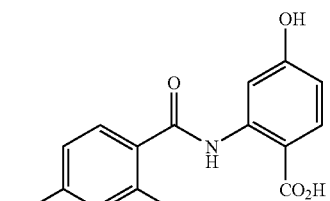

34

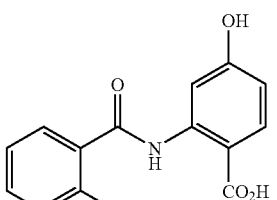

35

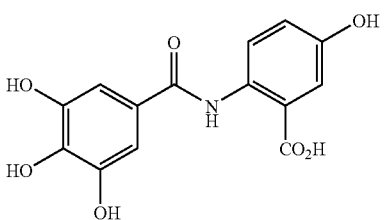

66

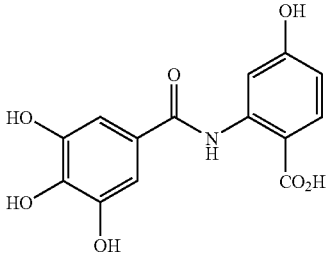

67

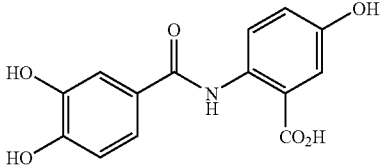

68

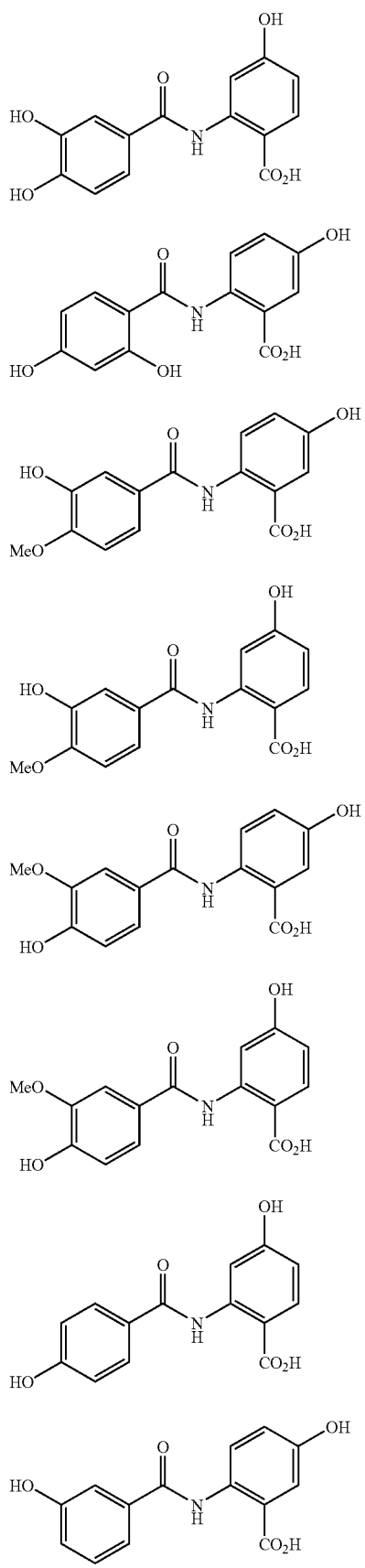
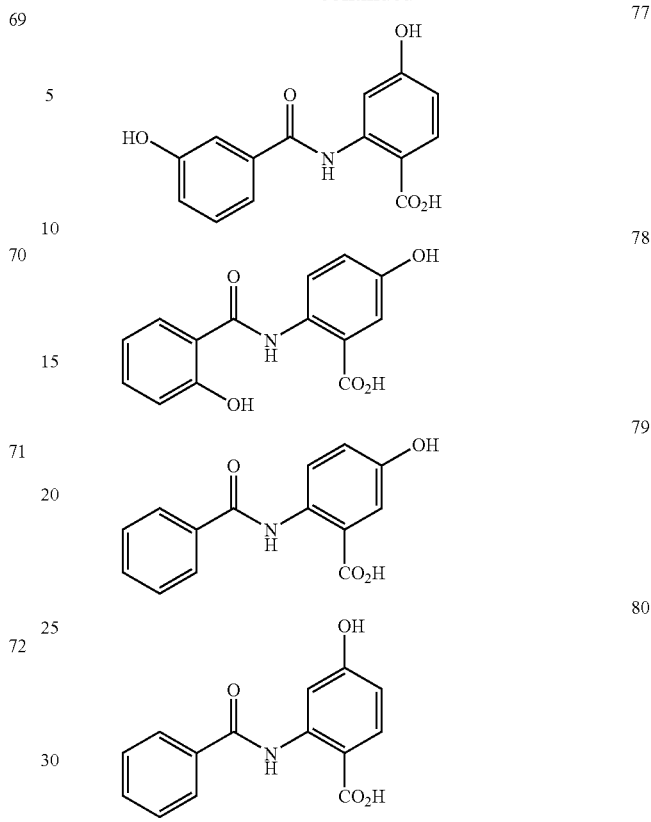

In the compounds described as particularly preferred and indicated by their structural formulae, $R^3$ is always H.

In place of these preferred compounds, it is also preferable in each case to use the corresponding compounds in which $R^3=CH_3$ or linear or branched alkyl having 2 to 30 C atoms.

Preferred individual antidandruff agents for use within the framework of the present invention are listed below.

Preferred antidandruff agents are climbazole and other azoles, e.g. benzimidazole, benzothiazole, bifonazole, butaconazole nitrate, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, thioconazole, diazoles and triazoles, e.g. terconazole and itraconazole, and any desired combinations of said azoles.

Other antidandruff agents which can be used are pyrithione salts, especially 1-hydroxy-2-pyrithione salts, preferred pyrithione salts being those of the metal cations of sodium, zinc, tin, calcium, magnesium, aluminum and zirconium. The zinc salt of 1-hydroxy-2-pyrithione (known as "zinc pyrithione" or "ZPT") is particularly preferred.

Other antidandruff agents include coal tar, sulfur, selenium sulfides, aluminum chloride, octopirox (INCI: Piroctone Olamine), cyclopiroxolamines, undecylenic acid and its metal salts, potassium permanganate, sodium thiosulfate, propylene glycol, other branched and unbranched aliphatic diols and polyols (e.g. 1,2-diols having 5-18 carbon atoms), urea preparations, griseofulvin, 8-hydroxyquinoline, ciloquinol, thiobendazole, thiocarbamates, triclosan, haloprogin, polyenes, hydroxypyridone, morpholine, benzylamine, allylamines (e.g. terbinafine), tea tree oil, clove oil, coriander oil, palmarosa oil, thyme oil and cinnamon oil, as well as ethereal oil of bitter orange, cinnamaldehyde, citronellic acid, farnesol, berberine, hinokitiol, tropolone, birch tar oils, ichthyol (sulfonated shale oil), Sensiva SC-50 (ethylhexyl glycerol), polyglycerol esters, e.g. polyglycerol-3 caprylate, arylalkyl alcohols, e.g. phenylethyl alcohol, 3-phenyl-1-propanol, vetikol (4-methyl-4-phenyl-2-pentanol), muguet alcohol (2,2-dimethyl-3-phenylpropanol), Elestab HP-100, azelaic acid, lyticase, isothiazalinones, e.g. octylisothiazalinone, iodopropynyl butyl carbamate (IPBC) and combinations of these active compounds.

Those skilled in the art can extend the following list with many other antidandruff agents; the antidandruff agents listed can also be used in combination with one another:

Antidandruff agents which are preferred on the basis of their particular synergistic effect are climbazole, zinc pyrithione, ichthyol and octopirox (INCI: Piroctone Olamine).

A very particularly preferred antidandruff agent is climbazole (trade name: Crinipan).

The mixtures according to the invention, especially those characterized as preferred, possess a synergistically intensified efficacy against itching. The efficacy of mixtures according to the invention is surprisingly superior to that of products exclusively comprising one or more compounds of Formula 1 (as indicated above) or exclusively comprising one antidandruff agent.

The mixtures according to the invention are particularly effective and furthermore are free of any toxicologically or dermatologically critical secondary components; they can therefore be used without problems in pharmaceutical or cosmetic products. In general, it is pointed out that, in the concentration range relevant to efficacy, the substances to be used in cosmetic and/or pharmaceutical products should be toxicologically safe,
should have a good skin tolerability,
should be stable (especially in the conventional cosmetic and/or pharmaceutical formulations),
should preferably be odorless and
should be inexpensive to prepare (i.e. by using standard processes and/or by starting from standard precursors).

These requirements are met by the mixtures according to the invention.

Although the use concentration of the compounds of Formula 1 to be used according to the invention can range from 0.0001 to 10 percent by weight—depending on the substance—as is already the case according to WO 2004/047833, it is preferable to use a low concentration of the compound(s) of Formula 1. A concentration range of 0.001 to 1 percent by weight is particularly preferred and a range of 0.01 to 0.2 percent by weight is very particularly preferred, based in each case on the total weight of a ready-to-use cosmetic or pharmaceutical end product.

Depending on the substance, the use concentration of the antidandruff agents to be used according to the invention ranges preferably from 0.01 to 20 percent by weight and particularly preferably from 0.1 to 5 percent by weight, based on the total weight of a ready-to-use cosmetic or pharmaceutical end product.

Particularly preferred mixtures according to the invention are those in which the weight ratio of the total amount of compounds of Formula 1 to the total amount of antidandruff agents ranges from 1:100 to 2:1, preferably from 1:50 to 1:1 and particularly preferably from 1:10 to 1:2. Thus the proportion by weight of antidandruff agents is preferably predominant compared with that of the compounds of Formula 1.

Particularly preferably, the weight ratio of the compound(s) of Formula 1 to the preferred antidandruff agents, especially climbazole and other azoles, pyrithione salts, particularly zinc pyrithione, ichthyol and octopirox, ranges from 1:100 to 2:1, preferably from 1:50 to 1:1 and particularly preferably from 1:10 to 1:2.

The mixtures according to the invention can be combined with a large number of other components to give preferred cosmetic and/or pharmaceutical mixtures or products.

Combination with Skin Moisture Regulators:

Itching occurs with particular intensity especially when the skin is dry. The use of skin moisture regulators in cosmetic and pharmaceutical products can significantly alleviate itching. The synergistically effective combinations according to the invention of compounds of Formula 1 (anthranilic acid amides) and antidandruff agents can therefore also be combined particularly advantageously with skin moisture regulators. Cosmetic preparations containing a mixture according to the invention can therefore advantageously also contain the following moisture retention regulators: sodium lactate, urea, urea derivatives, alcohols, glycerol, diols such as propylene glycol, hexylene glycol, 1,2-pentanediol, 1,2-hexanediol, 1,2-heptanediol, 1,2-octanediol, 1,2-nonanediol, 1,2-decanediol or mixtures of said diols, especially mixtures of 1,2-hexanediol and 1,2-octanediol, collagen, elastin or hyaluronic acid, diacyl adipates, petrolatum, urocanic acid, lecithin, panthenol, phytantriol, lycopene, (pseudo-)ceramides, glycosphingolipids, cholesterol, phytosterols, chitosan, chondroitin sulfate, lanolin, lanolin esters, amino acids, alpha-hydroxy acids (e.g. citric acid, lactic acid, malic acid) and derivatives thereof, mono-, di- and oligosaccharides such as glucose, galactose, fructose, mannose, fructose and lactose, polysugars such as β-glucans, especially 1,3-1,4-β-glucan from oats, alpha-hydroxy fatty acids, triterpene acids such as betulinic acid or ursolic acid, and algae extracts.

Depending on the substance, the use concentration of the moisture retention regulators ranges from 0.1 to 10% (m/m) and preferably from 0.5 to 5% (m/m), based on the total weight of a ready-to-use cosmetic or pharmaceutical end product. These data apply especially to diols that are advantageously to be used, such as hexylene glycol, 1,2-pentanediol, 1,2-hexanediol, 1,2-octanediol and 1,2-decanediol, as well as mixtures of 1,2-hexanediol and 1,2-octanediol.

Combination with Cooling Agents:

The use of cooling agents in cosmetic and pharmaceutical products can alleviate itching. The synergistically effective combinations according to the invention of compounds of Formula 1 (anthranilic acid amides) and antidandruff agents can therefore additionally be combined particularly advantageously with cooling agents. Preferred individual cooling agents for use within the framework of the present invention are listed below. Those skilled in the art can add a large number of other cooling agents to this list; the cooling agents listed can also be used in combination with one another: l-menthol, d-menthol, racemic menthol, menthone glycerol acetal (trade name: Frescolat® MGA), menthyl lactate (trade name: Frescolat® ML; menthyl lactate is preferably l-menthyl lactate, especially l-menthyl l-lactate), substituted menthyl-3-carboxamides (e.g. menthyl-3-carboxylic acid N-ethylamide), 2-isopropyl-N-2,3-trimethylbutanamide, substituted cyclohexanecarboxamides, 3-menthoxypropane-1,2-diol, 2-hydroxyethyl menthyl carbonate, 2-hydroxypropyl menthyl carbonate, N-acetylglycine menthyl ester, isopulegol, hydroxycarboxylic acid menthyl esters (e.g. menthyl 3-hydroxybutyrate), monomenthyl succinate, 2-mercaptocyclodecanone, menthyl 2-pyrrolidin-5-onecarboxylate, 2,3-dihydroxy-p-menthane, 3,3,5-trimethylcyclohexanone glycerol ketal, 3-menthyl-3,6-di- and trioxaalkanoates, 3-menthyl methoxyacetate and icilin.

Cooling agents that are preferred on the basis of their particular synergistic effect are l-menthol, d-menthol, racemic menthol, menthone glycerol acetal (trade name: Frescolat® MGA), menthyl lactate (preferably l-menthyl lactate, especially l-menthyl l-lactate (trade name: Frescolat® ML)), substituted menthyl-3-carboxamides (e.g. menthyl-3-carboxylic acid N-ethylamide), 2-isopropyl-N-2,3-trimethylbutanamide, substituted cyclohexanecarboxamides, 3-menthoxypropane-1,2-diol, 2-hydroxyethyl menthyl carbonate, 2-hydroxypropyl menthyl carbonate and isopulegol.

Particularly preferred cooling agents are l-menthol, racemic menthol, menthone glycerol acetal (trade name: Frescolat® MGA), menthyl lactate (preferably l-menthyl lactate, especially l-menthyl l-lactate (trade name: Frescolat® ML)), 3-menthoxypropane-1,2-diol, 2-hydroxyethyl menthyl carbonate and 2-hydroxypropyl menthyl carbonate.

Very particularly preferred cooling agents are l-menthol, menthone glycerol acetal (trade name: Frescolat® MGA) and menthyl lactate (preferably l-menthyl lactate, especially l-menthyl l-lactate (trade name: Frescolat® ML)).

Depending on the substance, the use concentration of the cooling agents to be used ranges preferably from 0.01 to 20 percent by weight and particularly preferably from 0.1 to 5 percent by weight, based on the total of a ready-to-use cosmetic or pharmaceutical end product.

Particularly preferred mixtures according to the invention are those in which the weight ratio of the total amount of compounds of Formula 1 to the total amount of cooling agents ranges from 1:100 to 1:2, preferably from 1:50 to 1:5 and particularly preferably from 1:30 to 1:10. Thus the proportion by weight of cooling agents is preferably predominant compared with that of the compounds of Formula 1.

Combination with Osmolytes:

The mixtures according to the invention can also be used together with osmolytes. Examples of osmolytes which may be mentioned are substances from the group comprising sugar alcohols (myoinositol, mannitol, sorbitol), quaternary amines such as taurine, choline, betaine, betaine glycine, ectoin, diglycerol phosphate, phosphorylcholine or glycerophosphorylcholines, amino acids such as glutamine, glycine, alanine, glutamate, aspartate or proline, phosphatidyl-choline, phosphatidylinositol, inorganic phosphates, and polymers of said compounds, such as proteins, peptides, polyamino acids and polyols. All osmolytes have a skin moisturizing action at the same time.

Combination with Keratolytic Substances:

Preferably, keratolytic substances can also be combined with the mixtures according to the invention. Keratolytic compounds include the large group of alpha-hydroxy acids. It is preferable to use salicylic acid, for example.

Combination with Nurturing Substances:

In formulations containing mixtures according to the invention for the topical cosmetic or pharmaceutical treatment of e.g. dry, itchy skin, a high proportion especially of nurturing substances is also of particular advantage because of the reduced transepidermal water loss due to lipophilic components. In one preferred embodiment the compositions contain one or more nurturing animal and/or vegetable fats and oils such as olive oil, sunflower oil, refined soya oil, palm oil, sesame oil, rapeseed oil, almond oil, borage oil, evening primrose oil, coconut oil, shea butter, jojoba oil, sperm oil, tallow, neatsfoot oil and lard, and optionally other nurturing components such as fatty alcohols having 8-30 C atoms. The fatty alcohols used here can be saturated or unsaturated and linear or branched.

Nurturing substances which can particularly preferably be combined with the mixtures according to the invention also include especially
- ceramides, which are understood as meaning N-acylsphingosines (fatty acid amides of sphingosine) or synthetic analogues of such lipids (so-called pseudo-ceramides) that markedly improve the water retention capacity of the stratum corneum;
- phospholipids, e.g. soya lecithin, egg lecithin and cephalins; and
- petrolatum, paraffin oils and silicone oils, the latter including, inter alia, dialkyl- and alkylarylsiloxanes such as dimethylpolysiloxane and methyl-phenylpolysiloxane, and their alkoxylated and quaternized derivatives.

Combination with Preservatives, Antiperspirants or Chelators:

Cosmetic preparations containing mixtures according to the invention can also contain active compounds for preserving cosmetic products, antiperspirants and (metal) chelators.

Combination with Animal and/or Vegetable Protein Hydrolyzates:

Animal and/or vegetable protein hydrolyzates can also advantageously be added to the mixtures according to the invention. The following are particularly advantageous in this context: fractions of elastin, collagen, keratin, lactalbumin, soya protein, oat protein, pea protein, almond protein and wheat protein, or corresponding protein hydrolyzates, and also their condensation products with fatty acids, as well as quaternized protein hydrolyzates, the use of vegetable protein hydrolyzates being preferred.

Combination with Solvents:

If a cosmetic or dermatological preparation containing synergistically effective combinations of anthranilic acid amides and antidandruff agents is a solution or lotion, the following solvents can be used:
- water or aqueous solutions;
- fatty oils, fats, waxes and other natural and synthetic fatty substances, preferably esters of fatty acids with alcohols of low C number, e.g. with isopropanol, propylene glycol or glycerol, or esters of fatty alcohols with alkanoic acids of low C number or with fatty acids;
- alcohols, diols or polyols of low C number and their ethers, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

Mixtures of the abovementioned solvents are used in particular. Water can be an additional component of alcoholic solvents.

Combination with Other Active Compounds:

Cosmetic preparations containing a mixture according to the invention can also particularly advantageously contain anti-inflammatory compounds and/or compounds that alleviate reddening and/or other compounds that alleviate itching, it being possible to use any anti-inflammatory compounds and/or compounds that alleviate reddening and/or itching which are suitable or conventionally used for cosmetic and/or dermatological applications. Steroidal anti-inflammatory substances of the corticosteroid type, e.g. hydrocortisone, hydrocortisone derivatives such as hydrocortisone 17-butyrate, dexamethasone, dexamethasone phosphate, methylprednisolone or cortisone, are advantageously used as anti-inflammatory compounds or compounds that alleviate reddening and/or itching; other steroidal anti-inflammatories can be added to the list. It is also possible to use non-steroidal anti-inflammatories. Examples which should be mentioned here are oxicams such as piroxicam or tenoxicam; salicylates such as aspirin, disalcid, solprin or fendosal; acetic acid derivatives such as diclofenac, fenclofenac, indomethacin, sulindac, tolmetin or clindanac; fenamates such as mefenamic, meclofenamic, flufenamic or niflumic; propionic acid derivatives such as ibuprofen, naproxen or benoxaprofen; or pyrazoles such as phenylbutazone, oxyphenylbutazone, febrazone or azapropazone. A possible alternative is to use natural anti-inflammatory substances or substances that alleviate reddening and/or itching. Plant extracts, special high-activity plant extract fractions and high-purity active substances isolated from plant extracts can be used. Particular preference is afforded to extracts, fractions and active substances from camomile, *Aloe vera*, *Commiphora* species, *Rubia* species, willow, willow-herb, oats, calendula, arnica, St John's wort, honeysuckle, rosemary, *Passiflora incarnata*, witch hazel, ginger or Echinacea, and pure substances such as, inter alia, (alpha-)bisabolol, apigenin, apigenin-7-glucoside, boswellic acid, phytosterols, glycyrrhizin, glabridin and licochalcone A. The synergistically effective combinations of anthranilic acid amides and antidandruff agents can also contain mixtures of two or more anti-inflammatory compounds.

Depending on the substance, the use concentration of the anti-inflammatory compounds which can be used ranges from 0.005 to 2% (m/m) and preferably from 0.05 to 0.5% (m/m), based on the total weight of a ready-to-use cosmetic or pharmaceutical end product. These data apply especially to bisabolol.

Combination with Antioxidants:

Cosmetic preparations containing a mixture according to the invention can also contain antioxidants, it being possible to use any antioxidants which are suitable or conventionally used for cosmetic and/or dermatological applications.

Combination with Vitamins:

Cosmetic preparations containing a mixture according to the invention can also contain vitamins and vitamin precursors, it being possible to use any vitamins or vitamin precursors which are suitable or conventionally used for cosmetic and/or dermatological applications.

Combination with Skin Lighteners:

In numerous cases the formulations according to the invention can advantageously be used in combination with skin lightening compounds, it being possible according to the invention to use any skin lightening compounds which are suitable or conventionally used for cosmetic and/or dermatological applications. Advantageous skin lightening compounds in this context are kojic acid (5-hydroxy-2-hydroxymethyl-4-pyranone), kojic acid derivatives, e.g. kojic acid dipalmitate, arbutin, ascorbic acid, ascorbic acid derivatives, hydroquinone, hydroquinone derivatives, resorcinol, sulfur-containing molecules, e.g. glutathione or cysteine, alpha-hydroxy acids (e.g. citric acid, lactic acid, malic acid) and derivatives thereof, N-acetyltyrosine and derivatives, undecenoyl-phenylalanine, gluconic acid, 4-alkylresorcinols, chromone derivatives such as aloesin, flavonoids, thymol derivatives, 1-aminoethylphosphinic acid, thiourea derivatives, ellagic acid, nicotinamide, zinc salts, e.g. zinc chloride or gluconate, thujaplicin and derivatives, triterpenes such as maslinic acid, sterols such as ergosterol, benzofuranones such as senkyunolide, vinyl- and ethylguaiacol, inhibitors of nitrogen oxide synthesis, e.g. L-nitroarginine and derivatives thereof, 2,7-dinitroindazole or thiocitrullin, metal chelators (e.g. α-hydroxy fatty acids, palmitic acid, phytic acid, lactoferrin, humic acid, gallic acid, bile extracts, bilirubin, biliverdin, EDTA, EGTA and derivatives thereof), retinoids, soy milk, serine protease inhibitors or lipoic acid, or other synthetic or natural active compounds for lightening the skin and hair, it also being possible for the latter to be used in the form of a plant extract, e.g. bearberry extract, rice extract, liquorice root extract or components obtained therefrom by enrichment, such as glabridin or licochalcone A, Artocarpus extract, extracts of *Rumex* and *Ramulus* species, extracts of pine species (*Pinus*) and extracts of *Vitis* species, or stilbene derivatives obtained therefrom by enrichment, and *Saxifraga*, mulberry, *Scutelleria* and/or grape extracts.

Combination with Skin Tanning Agents:

Cosmetic preparations containing a mixture according to the invention can also contain compounds with a skin tanning action, it being possible in this context to use any skin tanning compounds which are suitable or conventionally used for cosmetic and/or dermatological applications. An example which may be mentioned here is dihydroxyacetone (DHA; 1,3-dihydroxy-2-propanone). DHA can exist in both monomeric and dimeric form, the proportion of dimer being predominant in the crystalline form.

Combination with Saccharides:

Cosmetic preparations containing a mixture according to the invention can also contain mono-, di- and oligosaccharides, e.g. glucose, galactose, fructose, mannose, fructose and lactose.

Combination with Plant Extracts:

Cosmetic preparations containing a mixture according to the invention can also contain plant extracts, which are conventionally prepared by extraction of the whole plant or, in specific cases, exclusively from the blossom and/or leaves, wood, bark or roots of the plant.

Combination with Surfactants:

Cosmetic preparations containing a mixture according to the invention can also contain anionic, cationic, non-ionic and/or amphoteric surfactants, especially when crystalline or microcrystalline solids, e.g. inorganic micropigments, are to be incorporated into the preparations. Surfactants are amphiphilic substances capable of solubilising organic, non-polar substances in water. The hydrophilic parts of a surfactant molecule are usually polar functional groups, e.g. $-COO^-$, $-OSO_3^{2-}$ or $-SO_3^-$, while the hydrophobic parts are normally non-polar hydrocarbon radicals. Surfactants are generally classified according to the type and charge of the hydrophilic part of the molecule. They can be divided into four groups:

anionic surfactants,
cationic surfactants,
amphoteric surfactants and
non-ionic surfactants.

Anionic surfactants normally contain carboxylate, sulfate or sulfonate groups as functional groups. In aqueous solution they form negatively charged organic ions in an acidic or neutral medium. Cationic surfactants are characterized virtually exclusively by the presence of a quaternary ammonium group. In aqueous solution they form positively charged organic ions in an acidic or neutral medium. Amphoteric surfactants contain both anionic and cationic groups and accordingly behave like anionic or cationic surfactants in aqueous solution, depending on the pH. They have a positive charge in a strongly acidic medium and a negative charge in an alkaline medium. In the neutral pH range, on the other hand, they are zwitterionic. Polyether chains are typical of non-ionic surfactants. Non-ionic surfactants do not form ions in an aqueous medium.

A. Anionic Surfactants

Anionic surfactants that can advantageously be used are acylamino acids (and salts thereof) such as
acylglutamates, e.g. sodium acylglutamate, di-TEA palmitoylaspartate and sodium caprylic/capric glutamate, acylpeptides, e.g. palmitoyl-hydrolyzed lactoprotein, sodium cocoyl-hydrolyzed soya protein and sodium/potassium cocoyl-hydrolyzed collagen, sarcosinates, e.g. myristoyl sarcosine, TEA lauroylsarcosinate, sodium lauroylsarcosinate and sodium cocoylsarcosinate, taurates, e.g. sodium lauroyltaurate and sodium methylcocoyltaurate, acyllactylates, lauroyllactylate, caproyllactylate and stearoyllactylate, alaninates;

carboxylic acids and derivatives, such as lauric acid, aluminum stearate, magnesium alkanolate and zinc undecylenate, ester-carboxylic acids, e.g. calcium stearoyllactylate, laureth-6 citrate and sodium PEG-4 lauramidocarboxylate, ether-carboxylic acids, e.g. sodium laureth-13 carboxylate and sodium PEG-6 cocamidocarboxylate;

phosphoric acid esters and salts, such as DEA oleth-10 phosphate and dilaureth-4 phosphate;

sulfonic acids and salts, such as acylisethionates, e.g. sodium/ammonium cocoylisethionate, alkylarylsulfonates, alkylsulfonates, e.g. sodium coco monoglyceride sulfate, sodium $C_{12-14}$-olefinsulfonate, sodium laurylsulfoacetate and magnesium PEG-3 cocamidosulfate, sulfosuccinates, e.g. sodium dioctylsulfosuccinate, disodium laureth sulfosuccinate, disodium laurylsulfosuccinate and disodium MEA undecylenamidosulfosuccinate;

and sulfuric acid esters such as alkyl ether sulfate, e.g. sodium, ammonium, magnesium, MIPA and TIPA laureth sulfate, sodium myreth sulfate and sodium C12-13 pareth sulfate, alkylsulfates, e.g. sodium, ammonium and TEA laurylsulfate.

B. Cationic Surfactants

Cationic surfactants that can advantageously be used are alkylamines, alkylimidazoles, ethoxylated amines and quaternary surfactants:

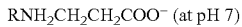

RNH$_2$CH$_2$CH$_2$COO$^-$ (at pH 7)

RNHCH$_2$CH$_2$COO$^-$B$^+$ (at pH 12),

B$^+$=arbitrary cation, e.g. Na$^+$ esterquats

Quaternary surfactants contain at least one N atom that is covalently bonded to 4 alkyl or aryl groups. This produces a positive charge, irrespective of the pH. Alkylbetaine, alkylamidopropylbetaine and alkylamidopropylhydroxysulfaine are advantageous. The cationic surfactants used can also preferably be selected from the group comprising quaternary ammonium compounds, in particular benzyltrialkylammonium chlorides or bromides, e.g. benzyldimethylstearylammonium chloride, and also alkyltrialkylammonium salts, e.g. cetyltrimethylammonium chloride or bromide, alkyldimethylhydroxyethylammonium chlorides or bromides, dialkyldimethylammonium chlorides or bromides, alkylamidoethyl-trimethylammonium ether sulfates, alkylpyridinium salts, e.g. lauryl- or cetyl-pyrimidinium chloride, imidazoline derivatives and compounds of a cationic nature, such as amine oxides, e.g. alkyldimethylamine oxides or alkylaminoethyl-dimethylamine oxides. Cetyltrimethylammonium salts can be used particularly advantageously.

C. Amphoteric Surfactants

Amphoteric surfactants that can advantageously be used are acyl-/dialkylethylenediamine, e.g. sodium acylamphoacetate, disodium acyl-amphodipropionate, disodium alkylamphodiacetate, sodium acylampho-hydroxypropylsulfonate, disodium acylamphodiacetate and sodium acyl-amphopropionate, N-alkylamino acids, e.g. aminopropylalkylglutamide, alkylaminopropionic acid, sodium alkylimidodipropionate and lauroamphocarboxyglycinate.

D. Non-Ionic Surfactants

Non-ionic surfactants that can advantageously be used are alcohols, alkanolamides such as cocamides MEA/DEA/MIPA, amine oxides such as cocamidopropylamine oxide, esters formed by the esterification of carboxylic acids with ethylene oxide, glycerol, sorbitan or other alcohols, ethers, e.g. ethoxylated/propoxylated alcohols, ethoxylated/propoxylated esters, ethoxylated/propoxylated glycerol esters, ethoxylated/propoxylated cholesterols, ethoxylated/propoxylated triglyceride esters, ethoxylated/propoxylated lanolin, ethoxylated/propoxylated polysiloxanes, propoxylated POE ethers, and alkyl polyglycosides such as lauryl glucoside, decyl glycoside and coco glycoside, sucrose esters and ethers, polyglycerol esters, diglycerol esters and monoglycerol esters, methyl glucose esters and esters of hydroxy acids.

The use of a combination of anionic and/or amphoteric surfactants with one or more non-ionic surfactants is also advantageous.

The surface-active substance can be present in a concentration of between 1 and 98% (m/m) in the preparations containing synergistically effective combinations of anthranilic acid amides and antidandruff agents, based on the total weight of the preparations.

Emulsions Comprising a Mixture According to the Invention:

Cosmetic or dermatological preparations containing synergistically effective combinations according to the invention of anthranilic acid amides and antidandruff agents can also take the form of emulsions.

The oily phase can advantageously be selected from the following group of substances:

mineral oils and mineral waxes;

fatty oils, fats, waxes and other natural and synthetic fatty substances, preferably esters of fatty acids with alcohols of low C number, e.g. with isopropanol, propylene glycol or glycerol, or esters of fatty alcohols with alkanoic acids of low C number or with fatty acids;

alkyl benzoates;

silicone oils such as dimethylpolysiloxanes, diethylpolysiloxanes, diphenyl-polysiloxanes and mixed forms thereof.

(a) Esters of saturated and/or unsaturated, branched and/or unbranched alkanecarboxylic acids having a chain length of 3 to 30 C atoms and saturated and/or unsaturated, branched and/or unbranched alcohols having a chain length of 3 to 30 C atoms, and (b) esters of aromatic carboxylic acids and saturated and/or unsaturated, branched and/or unbranched alcohols having a chain length of 3 to 30 C atoms, can advantageously be used. Preferred ester oils are isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 3,5,5-trimethylhexyl 3,5,5-trimethylhexanoate, 2-ethylhexyl isononanoate, 2-ethylhexyl 3,5,5-trimethylhexanoate, 2-ethylhexyl 2-ethylhexanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semisynthetic and natural mixtures of such esters, e.g. jojoba oil.

Furthermore, the oily phase can advantageously be selected from the group comprising branched and unbranched hydrocarbons and waxes, silicone oils, dialkyl ethers, the group comprising saturated or unsaturated, branched or unbranched alcohols, and also fatty acid triglycerides, specifically the triglycerol esters of saturated and/or unsaturated, branched and/or unbranched alkanecarboxylic acids having a chain length of 8 to 24 and especially 12 to 18 C atoms. The fatty acid triglycerides can advantageously be selected from the group comprising synthetic, semisynthetic and natural oils, e.g. olive oil, sunflower oil, soya oil, groundnut oil, rapeseed oil, almond oil, palm oil, coconut oil, palm kernel oil and the like. Arbitrary mixtures of such oil and wax components can also advantageously be used. In some cases it is also advantageous to use waxes, e.g. cetyl palmitate, as the sole lipid component of the oily phase; advantageously, the oily phase is selected from the group comprising 2-ethylhexyl isostearate, octyldodecanol, isotridecyl isononanoate, isoeicosane, 2-ethylhexyl cocoate, $C_{12-15}$-alkyl benzoate, caprylic/capric triglyceride and dicaprylyl ether. Mixtures of $C_{12-15}$-alkyl benzoate and 2-ethylhexyl isostearate, mixtures of $C_{12-15}$-alkyl benzoate and isotridecyl isononanoate and mixtures of $C_{12-15}$-alkyl benzoate, 2-ethylhexyl isostearate and isotridecyl isononanoate are particularly advantageous. The hydrocarbons paraffin oil, squalane and squalene can also advantageously be used. Advantageously, the oily phase can further contain cyclic or linear silicone oils or consist entirely of such oils, although it is preferable to use other oily phase components in addition to the silicone oil(s). Cyclomethicone (e.g. decamethylcyclopentasiloxane) can advantageously be used as a silicone oil. However, other silicone oils can also advantageously be used, examples being undecamethylcyclotrisiloxane, poly-dimethylsiloxane and poly(methylphenylsiloxane). Furthermore, mixtures of cyclomethicone and isotridecyl isononanoate and of cyclomethicone and 2-ethylhexyl isostearate are particularly advantageous.

The aqueous phase of preparations that contain synergistically effective combinations of anthranilic acid amides and antidandruff agents and take the form of an emulsion can advantageously comprise alcohols, diols or polyols of low C number, as well as ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, and also alcohols of low C number, e.g. ethanol, isopropanol, 1,2-propanediol and glycerol, and in particular one or more thickeners, which can advantageously be selected from the group comprising silicon dioxide, aluminum silicates, polysaccharides and derivatives thereof, e.g. hyaluronic acid, xanthan gum, hydroxypropyl methyl cellulose, and particularly advantageously from the group comprising polyacrylates, preferably a polyacrylate from the group comprising the so-called carbopols, e.g. carbopols of types 980, 981, 1382, 2984 and 5984, in each case on their own or in combination.

Preparations that contain synergistically effective combinations of anthranilic acid amides and antidandruff agents and take the form of an emulsion advantageously comprise one or more emulsifiers. O/W emulsifiers can, for example, advantageously be selected from the group comprising polyethoxylated or polypropoxylated or polyethoxylated and polypropoxylated products, e.g.:

fatty alcohol ethoxylates,
ethoxylated wool wax alcohols,
polyethylene glycol ethers of the general formula

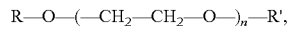
R—O—(—CH$_2$—CH$_2$—O—)$_n$—R', fatty acid ethoxylates of the general formula R—COO—(—CH$_2$—CH$_2$—O—)$_n$—H, etherified fatty acid ethoxylates of the general formula

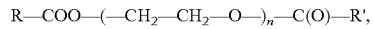
R—COO—(—CH$_2$—CH$_2$—O—)$_n$—C(O)—R', esterified fatty acid ethoxylates of the general formula

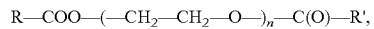
R—COO—(—CH$_2$—CH$_2$—O—)$_n$—C(O)—R', polyethylene glycol glycerol fatty acid esters,
ethoxylated sorbitan esters,
cholesterol ethoxylates,
ethoxylated triglycerides,
alkyl ether carboxylic acids of the general formula R—COO—(—CH$_2$—CH$_2$—O—)$_n$—OOH, where n is a number from 5 to 30,
polyoxyethylene sorbitol fatty acid esters,
alkyl ether sulfates of the general formula R—O—(—CH$_2$—CH$_2$—O—)$_n$—SO$_3$—H, fatty alcohol propoxylates of the general formula R—O—(—CH$_2$—CH(CH$_3$)—O—)$_n$—H, polypropylene glycol ethers of the general formula R—O—(—CH$_2$—CH(CH$_3$)—O—)$_n$—R', propoxylated wool wax alcohols,
etherified fatty acid propoxylates R—COO—(—CH$_2$—CH(CH$_3$)—O—)$_n$—R', esterified fatty acid propoxylates of the general formula R—COO—(—CH$_2$—CH(CH$_3$)—O—)$_n$—C(O)—R', fatty acid propoxylates of the general formula R—COO—(—CH$_2$—CH(CH$_3$)—O—)$_n$—H, polypropylene glycol glycerol fatty acid esters,
propoxylated sorbitan esters,
cholesterol propoxylates,
propoxylated triglycerides,
alkyl ether carboxylic acids of the general formula R—O—(—CH$_2$—CH(CH$_3$)—O—)$_n$—CH$_2$—COOH, alkyl ether sulfates and the acids on which these sulfates are based of the general formula R—O—(—CH$_2$—CH(CH$_3$)—O—)$_n$—SO$_3$—H, fatty alcohol ethoxylates/propoxylates of the general formula R—O—X$_n$—Y$_m$—H, polypropylene glycol ethers of the general formula R—O—X$_n$—Y$_m$—R', etherified fatty acid propoxylates of the general formula R—COO—X$_n$—Y$_m$—R', fatty acid ethoxylates/propoxylates of the general formula R—COO—X$_n$—Y$_m$—H.

According to the invention, the polyethoxylated or polypropoxylated or polyethoxylated and polypropoxylated O/W emulsifiers used are particularly advantageously selected from the group comprising substances having HLB values of 11-18, very particularly advantageously having HLB values of 14.5-15.5, if the O/W emulsifiers contain saturated radicals R and R'. If the O/W emulsifiers contain unsaturated radicals R and/or R', or if isoalkyl derivatives are present, the preferred HLB value of such emulsifiers can also be lower or higher. It is advantageous to select the fatty alcohol ethoxylates from the group comprising ethoxylated stearyl alcohols, cetyl alcohols and cetylstearyl alcohols (cetearyl alcohols). The following are particularly preferred:

polyethylene glycol (13) stearyl ether (steareth-13), polyethylene glycol (14) stearyl ether (steareth-14), polyethylene glycol (15) stearyl ether (steareth-15), polyethylene glycol (16) stearyl ether (steareth-16), polyethylene glycol (17) stearyl ether (steareth-17), polyethylene glycol (18) stearyl ether (steareth-18), polyethylene glycol (19) stearyl ether (steareth-19), polyethylene glycol (20) stearyl ether (steareth-20), polyethylene glycol (12) isostearyl ether (isosteareth-12), polyethylene glycol (13) isostearyl ether (isosteareth-13), polyethylene glycol (14) isostearyl ether (isosteareth-14), polyethylene glycol (15) isostearyl ether (isosteareth-15), polyethylene glycol (16) isostearyl ether (isosteareth-16), polyethylene glycol (17) isostearyl ether (isosteareth-17), polyethylene glycol (18) isostearyl ether (isosteareth-18), polyethylene glycol (19) isostearyl ether (isosteareth-19), polyethylene glycol (20) isostearyl ether (isosteareth-20), polyethylene glycol (13) cetyl ether (ceteth-13), polyethylene glycol (14) cetyl ether (ceteth-14), polyethylene glycol (15) cetyl ether (ceteth-15), polyethylene glycol (16) cetyl ether (ceteth-16), polyethylene glycol (17) cetyl ether (ceteth-17), polyethylene glycol (18) cetyl ether (ceteth-18), polyethylene glycol (19) cetyl ether (ceteth-19), polyethylene glycol (20) cetyl ether (ceteth-20), polyethylene glycol (13) isocetyl ether (isoceteth-13), polyethylene glycol (14) isocetyl ether (isoceteth-14), polyethylene glycol (15) isocetyl ether (isoceteth-15), polyethylene glycol (16) isocetyl ether (isoceteth-16), polyethylene glycol (17) isocetyl ether (isoceteth-17), polyethylene glycol (18) isocetyl ether (isoceteth-18), polyethylene glycol (19) isocetyl ether (isoceteth-19), polyethylene glycol (20) isocetyl ether (isoceteth-20), polyethylene glycol (12) oleyl ether (oleth-12), polyethylene glycol (13) oleyl ether (oleth-13), polyethylene glycol (14) oleyl ether (oleth-14), polyethylene glycol (15) oleyl ether (oleth-15), polyethylene glycol (12) lauryl ether (laureth-12), polyethylene glycol (12) isolauryl ether (isolaureth-12), polyethylene glycol (13) cetylstearyl ether (ceteareth-13), polyethylene glycol (14) cetylstearyl ether (ceteareth-14), polyethylene glycol (15) cetylstearyl ether (ceteareth-15), polyethylene glycol (16) cetylstearyl ether (ceteareth-16), polyethylene glycol (17) cetylstearyl ether (ceteareth-17), polyethylene glycol (18) cetylstearyl ether (ceteareth-18), polyethylene glycol (19) cetylstearyl ether (ceteareth-19) and polyethylene glycol (20) cetylstearyl ether (ceteareth-20).

It is also advantageous to select the fatty acid ethoxylates from the following group:

polyethylene glycol (20) stearate, polyethylene glycol (21) stearate, polyethylene glycol (22) stearate, polyethylene glycol (23) stearate, polyethylene glycol (24) stearate, polyethylene glycol (25) stearate, polyethylene glycol (12) isostearate, polyethylene glycol (13) isostearate, polyethylene glycol (14) isostearate, polyethylene glycol (15) isostearate, polyethylene glycol (16) isostearate, polyethylene glycol (17) isostearate, polyethylene glycol (18) isostearate, polyethylene glycol (19) isostearate, polyethylene glycol (20) isostearate, polyethylene glycol (21) isostearate, polyethylene glycol (22) isostearate, polyethylene glycol (23) isostearate, polyethylene glycol (24) isostearate, polyethylene glycol (25) isostearate, polyethylene glycol (12) oleate, polyethylene glycol (13) oleate, polyethylene glycol (14) oleate, polyethylene glycol (15) oleate, polyethylene glycol (16) oleate, polyethylene glycol (17) oleate, polyethylene glycol (18) oleate, polyethylene glycol (19) oleate and polyethylene glycol (20) oleate.

Sodium laureth-11 carboxylate can advantageously be used as an ethoxylated alkyl ether carboxylic acid or a salt thereof. Sodium laureth 1-4 sulfate can advantageously be used as an alkyl ether sulfate. Polyethylene glycol (30) cholesteryl ether can advantageously be used as an ethoxylated cholesterol derivative. Polyethylene glycol (25) soyasterol has also proved useful.

Polyethylene glycol (60) evening primrose glycerides can advantageously be used as ethoxylated triglycerides.

It is also advantageous to select the polyethylene glycol glycerol fatty acid esters from the group comprising polyethylene glycol (20) glyceryl laurate, polyethylene glycol (21) glyceryl laurate, polyethylene glycol (22) glyceryl laurate, polyethylene glycol (23) glyceryl laurate, polyethylene glycol (6) glyceryl caprylate/caprate, polyethylene glycol (20) glyceryl oleate, polyethylene glycol (20) glyceryl isostearate and polyethylene glycol (18) glyceryl oleate/cocoate.

It is likewise favorable to select the sorbitan esters from the group comprising polyethylene glycol (20) sorbitan monolaurate, polyethylene glycol (20) sorbitan monostearate, polyethylene glycol (20) sorbitan monoisostearate, polyethylene glycol (20) sorbitan monopalmitate and polyethylene glycol (20) sorbitan monooleate.

The following can be used as advantageous W/O emulsifiers: fatty alcohols having 8 to 30 carbon atoms, monoglycerol esters of saturated and/or unsaturated, branched and/or unbranched alkanecarboxylic acids having a chain length of 8 to 24, in particular 12 to 18 C atoms, diglycerol esters of saturated and/or unsaturated, branched and/or unbranched alkanecarboxylic acids having a chain length of 8 to 24, in particular 12 to 18 C atoms, monoglycerol ethers of saturated and/or unsaturated, branched and/or unbranched alcohols having a chain length of 8 to 24, in particular 12 to 18 C atoms, diglycerol ethers of saturated and/or unsaturated, branched and/or unbranched alcohols having a chain length of 8 to 24, in particular 12 to 18 C atoms, propylene glycol esters of saturated and/or unsaturated, branched and/or unbranched alkanecarboxylic acids having a chain length of 8 to 24, in particular 12 to 18 C atoms, and sorbitan esters of saturated and/or unsaturated, branched and/or unbranched alkanecarboxylic acids having a chain length of 8 to 24, in particular 12 to 18 C atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprate and glyceryl monocaprylate.

Preferred Formulations:

The mixtures according to the invention can be incorporated without difficulty into conventional cosmetic or dermatological/keratological formulations such as, inter alia, pump sprays, aerosol sprays, creams, shampoos, ointments, tinctures, lotions, nail care products (e.g. nail varnishes, nail varnish removers, nail balsams) and the like. In this context it is also possible, and in some cases advantageous, to combine the synergistically effective combinations of anthranilic acid amides and antidandruff agents with other active compounds. In this context the cosmetic and/or dermatological/keratological formulations containing synergistically effective combinations of anthranilic acid amides and antidandruff agents can otherwise be of conventional composition and be used for treatment of the skin and/or hair in the sense of a dermatological/keratological treatment or a treatment in the sense of care cosmetics. However, the synergistically effective combinations of anthranilic acid amides and antidandruff agents can also be used in make-up products in decorative cosmetics.

Combination with Sunscreens:

For use, the cosmetic and/or dermatological/keratological formulations containing a mixture according to the invention are applied to the skin and/or hair in an adequate amount in the manner conventionally used for cosmetics and dermatological products. In this context cosmetic and dermatological preparations that contain a mixture according to the invention and additionally act as a sunscreen also offer particular advantages. Advantageously, these preparations contain at least one UVA filter and/or at least one UVB filter and/or at least one inorganic pigment. In this case the preparations can take various forms such as those conventionally employed for preparations of this type. Thus they can be e.g. a solution, an emulsion of the water-in-oil (W/O) type or of the oil-in-water (O/W) type or a multiple emulsion, e.g. of the water-in-oil-in-water (W/O/W) type, a gel, a hydrodispersion, a solid stick or else an aerosol.

Combination with Cosmetic Auxiliaries:

In cosmetic preparations, the mixtures according to the invention can advantageously also be combined with cosmetic auxiliaries such as those conventionally used in such preparations, e.g. antioxidants, perfume oils, antifoams, colorants, pigments with a coloring action, thickeners, surface-active substances, emulsifiers, plasticizers, other moisturizing and/or moisture-retaining substances, fats, oils, waxes or other conventional components of a cosmetic formulation, such as alcohols, polyols, polymers, foam stabilizers, electrolytes, organic solvents or silicone derivatives. According to the invention, any conceivable antioxidants, perfume oils, antifoams, colorants, pigments with a coloring action, thickeners, surface-active substances, emulsifiers, plasticizers, moisturizing and/or moisture-retaining substances, fats, oils, waxes, alcohols, polyols, polymers, foam stabilizers, electrolytes, organic solvents or silicone derivatives that are suitable or conventionally used for cosmetic and/or dermatological applications can be used here.

As regards other cosmetic and pharmaceutical active compounds, bases and auxiliaries which can particularly preferably be combined with the synergistically effective combinations according to the invention of anthranilic acid amides and antidandruff agents, reference may be made to the detailed descriptions in WO 2004/047833 and WO 03/069994.

Combination with Perfumes:

The mixtures according to the invention can also be used as a component of perfume compositions for hair and scalp care products and, especially because of their specific efficacy, can impart an additional itch-alleviating or antiallergic property e.g. to a perfumed finished product. Particularly preferred perfume compositions comprise (a) a sensorially effective amount of a perfume, (b) an itch-regulating, antiallergic and/or hyposensitizing amount of a synergistically effective mixture of anthranilic acid amides and antidandruff agents, and (c) optionally one or more excipients and/or additives. Since the proportion of perfume in a cosmetic finished product is frequently in the region of approx. 1% (m/m), a perfume containing a compound of Formula 1 according to the invention will preferably contain about 0.1-10% (m/m) of one or more compounds of Formula 1. It has proved particularly advantageous that the synergistically effective combinations of anthranilic acid amides and antidandruff agents have only a weak inherent odor or are even completely odorless, since this property predestines them in particular for use in a perfume composition.

Preferred embodiments of the mixtures according to the invention and of the processes and uses according to the invention can be seen from the following examples and corresponding tables:

EXAMPLES

The intensification of the itch-alleviating efficacy of the active compound combinations according to the invention is apparent from the human in vivo studies described below. Unless indicated otherwise, all the amounts are given in % by weight.

Example 1

Detection of the intensified efficacy of a shampoo formulation consisting of an itch-alleviating compound (dihydroavenanthramide D; CARN: 697235-49-7; 2-[[3-(4-hydroxyphenyl)-1-oxopropyl]amino]benzoic acid (9Cl)) and an antidandruff agent (climbazole; Symrise trade name: Crinipan) compared with a shampoo formulation containing only an antidandruff agent (climbazole; Symrise trade name: Crinipan)

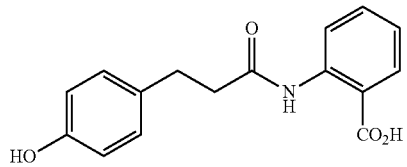

structural formula: dihydroavenanthramide D (= compound 8)

Description of the Test Method:

The tests were carried out on 24 subjects.

Samples:

1. Shampoo formulation 1 containing 0.2% by weight of the antidandruff compound climbazole (sample reference: GS05053SL-A)

2. Shampoo formulation 2 containing 0.2% by weight of the antidandruff compound climbazole and 0.05% of the itch-alleviating compound dihydroavenanthramide D (sample reference: GS05053SL-C)

Formulations

| Raw materials: | INCI name | % by weight | |
|---|---|---|---|
| | | GS05053SL A 0.2% of climbazole | GS05053SL C 0.2% of climbazole and 0.05% of dihydroaven-anthramide D |
| A. Crinipan AD | Climbazole | 0.2 | 0.2 |
| Butylene glycol | Butylene Glycol | 0.5 | — |
| Hydrolite-5 | Pentylene Glycol | 0.5 | — |
| Dragocid liquid | Phenoxyethanol Methyl-, Ethyl-, Butyl-, Propyl-, Isobutylparaben | 0.5 | 0.5 |
| B. Water, demineralized | Water (Aqua) | Ad 100 | Ad 100 |
| Sodium chloride | Sodium Chloride | 0.8 | 0.8 |
| Plantacare PS 10 | Sodium Laureth Sulfate (and) Lauryl Glycoside | 20.0 | 20.0 |
| Dihydroaven-anthramide D | Dihydro-avenanthramide D | — | 0.05 |
| Dehyton K | Cocoamidopropyl Betaine | 8.0 | 8.0 |
| C. Citric acid, 10% solution | Citric Acid | 1.0 | 1.0 |
| Total | | 100.0 | 100.0 |
| pH: | | 6.0 | 6.0 |

Experimental Procedure

A. Preconditioning

The subjects were preconditioned over a period of 14 days, during which they used a standard shampoo not containing active compounds. The application of other cosmetic agents to the scalp was not permitted during this period.

B. Test Period 12 subjects used shampoo GS05053SL-A and 12 used shampoo GS05053SL-C over a total test period of 42 days. The hair and scalp were treated once every other day with the appropriate product.

Test parameter: reduction of itching (subjective feeling of the subjects)

TABLE 1

Detection of the intensified efficacy of a shampoo formulation consisting of an itch-alleviating compound (dihydroaven-anthramide D) and an antidandruff agent (climbazole; Symrise trade name: Crinipan) compared with a shampoo formulation containing only an antidandruff agent

| | start | after 21 days | after 42 days |
|---|---|---|---|
| GS05053SL-A | 4 | 3.7 | 3.5 |
| GS05053SL-C | 4.1 | 3.3 | 2.4 |

Itching scale:
1 (no itching);
2 (slight);
3 (moderate);
4 (intense);
5 (very intense);
6 (extremely intense)

C. Result:

1. Product GS05053SL-A shows only a low efficacy in the reduction of itching.

Product GS05053SL-C shows a significantly better efficacy than product GS05053SL-A in the reduction of itching (Table 1). The intensity of itching could be reduced to a value of 2.4 after 42 days with product GS05053SL-C.

Example 2

Detection of the synergistically intensified efficacy of a shampoo formulation consisting of an itch-alleviating compound (dihydroavenanthramide D) and an antidandruff agent (climbazole; Symrise trade name: Crinipan) compared with a shampoo formulation containing only an antidandruff agent (climbazole; Symrise trade name: Crinipan) and compared with a shampoo formulation containing only an itch-alleviating compound (dihydroavenanthramide D)

Description of the Test Method:

The tests were carried out on 36 subjects.

Samples:

1. Shampoo formulation A containing 0.4% by weight of the antidandruff compound climbazole (sample reference: GS05053SL-A)
2. Shampoo formulation B containing 0.1% by weight of the itch-alleviating compound dihydroavenanthramide D (sample reference: GS05053SL-B)
3. Shampoo formulation C containing 0.2% by weight of the antidandruff compound climbazole and 0.05% of the itch-alleviating compound dihydroavenanthramide D (sample reference: GS05053SL-C)

Formulations

| Raw materials: | INCI name | % by weight | | |
|---|---|---|---|---|
| | | GS05098SL A 0.4% of climbazole | GS05098SL B 0.10% of dihydroaven-anthramide D | GS05098SL C 0.2% of climbazole 0.05% of dihydroaven-anthramide D |
| A. Crinipan AD | Climbazole | 0.4 | — | 0.2 |
| Butylene glycol | Butylene Glycol | 0.5 | — | — |
| Hydrolite-5 | Pentylene Glycol | 0.5 | — | — |
| Dragocid liquid | Phenoxyethanol Methyl-, Ethyl-, Butyl-, Propyl-, Isobutylparaben | 0.5 | 0.5 | 0.5 |
| B. Water, demineralized | Water (Aqua) | Ad 100 | Ad 100 | Ad 100 |
| Sodium chloride | Sodium Chloride | 0.8 | 0.8 | 0.8 |
| Plantacare PS 10 | Sodium Laureth Sulfate (and) Lauryl Glycoside | 20.0 | 20.0 | 20.0 |

-continued

|  |  | % by weight | | |
|---|---|---|---|---|
| Raw materials: | INCI name | GS05098SL A 0.4% of climbazole | GS05098SL B 0.10% of dihydroaven-anthramide D | GS05098SL C 0.2% of climbazole 0.05% of dihydroaven-anthramide D |
| Dihydroavenanthramide D (compound 8) | Dihydro-avenanthramide D | — | 0.1 | 0.05 |
| Dehyton K | Cocoamidopropyl Betaine | 8.0 | 8.0 | 8.0 |
| C. Citric acid, 10% solution | Citric Acid | 1.0 | 1.0 | 1.0 |
|  | Total | 100.0 | 100.0 | 100.0 |
|  | pH: | 6.0 | 6.0 | 6.0 |

Experimental Procedure

A. Preconditioning

The subjects were preconditioned over a period of 14 days, during which they used a standard shampoo not containing active compounds. The application of other cosmetic agents to the scalp was not permitted during this period.

B. Test Period 12 subjects used shampoo GS05098SL-A, 12 used shampoo GS05098SL-B and 12 used shampoo GS05098SL-C over a total test period of 42 days. The hair and scalp were treated once every other day with the appropriate product.

Test parameter: reduction of itching (subjective feeling of the subjects)

TABLE 2

Detection of the synergistically intensified efficacy of a shampoo formulation consisting of an itch-alleviating compound (dihydroavenanthramide D) and an antidandruff agent(climbazole; Symrise trade name: Crinipan) compared with a shampoo formulation containing only an antidandruff agent and compared with a formulation containing only an itch-alleviating compound

|  | start | after 21 days | after 42 days |
|---|---|---|---|
| GS05098SL-A | 4.1 | 3.8 | 3.4 |
| GS05098SL-B | 4.0 | 3.4 | 2.9 |

TABLE 2-continued

Detection of the synergistically intensified efficacy of a shampoo formulation consisting of an itch-alleviating compound (dihydroavenanthramide D) and an antidandruff agent(climbazole; Symrise trade name: Crinipan) compared with a shampoo formulation containing only an antidandruff agent and compared with a formulation containing only an itch-alleviating compound

|  | start | after 21 days | after 42 days |
|---|---|---|---|
| GS05098SL-C | 4.2 | 3.2 | 2.4 |

Itching scale:
1 (no itching);
2 (slight);
3 (moderate);
4 (intense);
5 (very intense);
6 (extremely intense)

C. Result:

Products GS05098SL-A and GS05098SL-B show a significantly lower efficacy than product GS05098SL-C in the reduction of itching. A synergistically intensified efficacy is proven below using the itching reduction factor after 42 days as an example. The calculated synergy index (SI, cf. Table 3) of 0.77 clearly shows that the mixture containing 0.05% of dihydroavenanthramide D and 0.2% of climbazole represents a synergistic combination of active compounds.

TABLE 3

Calculation of the synergy index (SI) after 42 days of a dihydroaven-anthramide D/climbazole mixture (product C) consisting of the comparative anti-dandruff compound (A) and the comparative itch-alleviating compound dihydro-avenanthramide D (product B)

| Alleviation of itching after 42 days | A GS05098SL-A Climbazole (0.4% by weight) | B GS05098SL-B Dihydroaven-anthramide D (0.1% by weight) | C GS05098SL-C Climbazole (0.2% by weight) and Dihydroaven-anthramide D (0.05% by weight) |
|---|---|---|---|
| Alleviation of itching (intensity scale: 1-6) 6 = extremely intense 1 = no itching Kull's equation: SI = C × D/A + C × E/B | 3.4 | 2.9 | 2.4 |
| Alleviation of itching: product A | 3.4 | | |
| Alleviation of itching: product B | 2.9 | | |
| Alleviation of itching: product C | 2.4 | | |
| D: proportion of A in C | 0.5 | | |
| E: proportion of B in C | 0.5 | | |
| SI: synergy index | 0.76 | | |

Literature: Synergy Index:
D. C. Steinberg; Cosmetics & Toiletries 115(11); pp 59-62 (2000)
F. C. Kull et al.; Applied Microbiology 9; pp 538-541 (1961)

Example 3

Formulations

Cosmetic formulations containing combinations according to the invention of antidandruff agents and itch-alleviating agents for the improved alleviation of itching are listed by way of example in Table 4.

Formulations:
1=antidandruff shampoo
2=2-in-1 shampoo
3=hair conditioner, leave on
4=hair conditioner, rinse off
5=hair setting gel
6=hair care spray, odor absorbing
7=hair oil
8=hair straightening cream

TABLE 4

| NAME OF RAW MATERIAL (Supplier) | INCI | 1 | 2 | 3 | 4 | 5 | 6 | 7 | 8 |
|---|---|---|---|---|---|---|---|---|---|
| Allantoin Merck | Allantoin | — | — | — | 0.1 | — | — | — | — |
| Aloe vera gel concentrate 10/1 (Symrise) | Water (Aqua), Aloe Barbadensis Leaf Juice | 1.0 | — | — | 0.5 | — | — | — | — |
| AMP-95 (Angus) | Aminomethyl-propanol | — | — | — | — | — | 0.7 | — | — |
| Antil 141 liquid (Degussa-Goldschmidt) | Propylene Glycol, PEG-55 Propylene Glycol Distearate | — | 1.0 | — | — | — | — | — | — |
| Antil 200 (Degussa-Goldschmidt) | PEG-200 Hydrogenated Glyceryl Palmitate, PEG-7 Glyceryl Cocoate | 1.5 | — | — | — | — | — | — | — |
| Bisabolol, linka alpha (Symrise) | Bisabolol | — | — | — | — | — | — | 0.2 | — |
| Carbopol ETD 2001 (Noveon) | Carbomer | — | — | — | — | 0.7 | — | — | — |
| Cetiol OE (Cognis) | Dicaprylyl Ether | — | — | 7.2 | — | — | — | — | — |
| Dracorin GMS (Symrise) | Glyceryl Stearate | — | — | — | — | — | — | — | 4.0 |
| Cetiol S (Cognis) | Diethylhexyl-cyclohexane | — | — | 7.0 | — | — | — | — | — |
| Cremogen AlphaPulp (Symrise) | Water (Aqua), Butylene Glycol, Malic Acid, Prunus Amygdalus Dulcis (Sweet Almond) Seed Extract, Actinidia Chinensis (Kiwi) Fruit Juice, Citrus Aurantium Dulcis (Orange) Juice, Citrus Paradisi (Grapefruit) Juice, Pyrus Malus (Apple) Juice, PEG-40 Hydrogenated Castor Oil | — | — | — | 1.0 | — | — | — | — |
| Crinipan AD | Climbazole | 0.5 | 0.5 | 0.1 | 0.5 | 0.3 | 0.5 | 0.5 | 0.5 |
| Dehyquart A CA (Cognis) | Cetrimonium Chloride | — | 1.0 | 4.0 | — | — | — | — | — |
| Dehyton K (Cognis) | Cocoamido-propyl Betaine | 6.0 | 8.0 | — | — | — | — | — | — |
| Dihydroavenanthramide D (Symrise) | Dihydroaven-anthramide D | 0.05 | 0.05 | 0.05 | 0.05 | 0.05 | 0.05 | 0.05 | 0.05 |
| D-Panthenol 75L (DSM Nutritional) | Panthenol | — | 1.0 | 1.0 | — | — | — | — | — |

TABLE 4-continued

| NAME OF RAW MATERIAL (Supplier) | INCI | FORMULATION [% BY WEIGHT] | | | | | | | |
|---|---|---|---|---|---|---|---|---|---|
| | | 1 | 2 | 3 | 4 | 5 | 6 | 7 | 8 |
| Dracorin CE | Glyceryl Stearate Citrate | — | — | — | 0.3 | — | — | — | — |
| Dracorin GOC (Symrise) | Glyceryl Oleate Citrate | — | — | — | 0.5 | — | — | — | — |
| Dracorin 100 s.e. P (Symrise) | PEG-100 Stearate, Glyceryl Stearate | — | — | 1.0 | — | — | — | — | 6.0 |
| Drago-Beta-Glucan (Symrise) | Water, Butylene Glycol, Glycerin, *Avena Sativa* (Oat) Kernel Extract | 0.3 | 0.3 | — | — | — | — | — | — |
| Dragocare W (Symrise) | PEG-40 Butyloctanol Wheat Germ Esters, Water (Aqua), Lactic Acid, Tocopherol | — | — | 0.5 | 1.0 | — | — | — | — |
| Dragocid liquid (Symrise) | Phenoxy-ethanol, Methyl-, Ethyl-, Butyl-, Propyl-, Isobutylparaben | 0.8 | 0.8 | 0.8 | 0.8 | 0.5 | — | — | — |
| Dragoderm (Symrise) | Glycerin, *Triticum Vulgare* (Wheat) Gluten, Water (Aqua) | 0.3 | 1.0 | — | 2.0 | — | — | — | — |
| Dragoxat 89 (Symrise) | Ethylhexyl Isononanoate | — | — | 1.0 | — | — | — | 5.0 | — |
| Emulsiphos (Symrise) | Potassium Cetyl Phosphate, Hydrogenated Palm Glycerides | — | — | 2.0 | — | — | — | — | — |
| Ethanol 96% | Ethanol | — | — | — | — | 30.0 | 30.0 | 0.3 | — |
| Eumulgin B1 (Cognis) | Ceteareth-12 | — | — | 3.5 | — | — | — | — | — |
| Euperlan PK 4000 (Cognis) | Glycol Distearate, Laureth-4, Cocoamido-propyl Betaine | 1.0 | 2.5 | — | — | — | — | — | — |
| Extrapon champagne GW (Symrise) | Water (Aqua), Glycerin, Wine Extract, Alcohol | — | — | 2.0 | — | — | — | — | — |
| Extrapone passion flower (Symrise) | Water (Aqua), Propylene Glycol, *Passiflora Incarnata* Extract, Glucose | 0.5 | — | — | — | — | — | — | — |
| Farnesol (Symrise) | Farnesol | — | — | — | — | — | 0.3 | 0.1 | — |
| Frescolat ML (Symrise) | Menthyl Lactate | — | — | — | — | 0.5 | 0.3 | 0.5 | — |
| Genapol LRO liquid (Clariant) | Sodium Laureth Sulfate | 35.0 | — | — | — | — | — | — | — |
| Glycerol, 99.5% | Glycerin | — | — | — | — | 10.0 | — | — | — |
| Hair conditioner base (Symrise) | Cetyl Alcohol, Behentrimonium Chloride, *Triticum Vulgare* (Wheat) Bran Extract, Linoleic Acid | — | — | — | 3.0 | — | — | — | — |
| Hydrolite-5 (Symrise) | Pentylene Glycol | — | — | 0.5 | 0.5 | 1.0 | — | — | — |
| Isoadipate (Symrise) | Diisopropyl Adipate | — | — | — | — | 0.5 | 0.3 | — | — |
| Isodragol (Symrise) | Triisononanoin | — | — | — | — | — | — | 1.0 | 3.0 |

TABLE 4-continued

| NAME OF RAW MATERIAL (Supplier) | INCI | 1 | 2 | 3 | 4 | 5 | 6 | 7 | 8 |
|---|---|---|---|---|---|---|---|---|---|
| PCL liquid 100 (Symrise) | Cetearyl Octanoate | — | — | — | — | — | 0.2 | — | 2.0 |
| Luviskol K 30 powder (BASF AG) | PVP | — | — | — | — | 3.0 | — | — | — |
| Luviskol VA 37 E (BASF AG) | PVP/VA Copolymer | — | — | — | — | — | — | 3.0 | — |
| Merquat 550 (Ondeo) | Polyquaternium-7 | 0.5 | 1.0 | — | — | — | — | — | — |
| Mineral oil | Mineral Oil | — | — | — | — | — | — | 88.8 | 3.0 |
| Mulsifan RT 203/80 (Z&S) | C12-15 Pareth-12 | — | — | — | — | 4.0 | — | — | — |
| Neo Heliopan AV (Symrise) | Ethylhexyl Methoxy-cinnamate | — | — | — | — | — | — | 0.5 | — |
| Neo Heliopan BB (Symrise) | Benzophenone-3 | 0.1 | 0.1 | — | — | — | 0.2 | — | — |
| Neo Heliopan Hydro (Symrise) | Phenyl-benzimidazole Sulfonic Acid | — | — | — | — | — | 0.2 | — | — |
| Neo-PCL water soluble N (Symrise) | Trideceth-9, PEG-5 Ethylhexanoate, Water (Aqua) | 1.0 | — | — | — | — | — | — | — |
| Neutral TE (BASF) | Tetrahydroxy-propyl Ethylenediamine | — | — | — | — | 1.0 | — | — | — |
| Polyquart H-81 (Cognis) | PEG-15 Cocopolyamine | — | — | 3.0 | — | — | — | — | — |
| PCL liquid 100 (Symrise) | Cetearyl Octanoate | — | — | — | 0.5 | — | — | — | — |
| Propylene glycol | Propylene Glycol | — | — | — | — | — | — | — | 5.0 |
| Rose CL forte (Symrise) | Water (Aqua), Glycerin, PEG-40 Hydrogenated Castor Oil, Rosa Damascena Flower Oil | — | 0.5 | — | — | — | — | — | — |
| Sodium chloride | Sodium Chloride | 0.8 | 0.5 | — | — | — | — | — | — |
| Sodium hydroxide, 20% sol. | Sodium Hydroxide | 0.2 | 0.1 | — | 0.2 | — | — | — | 8.0 |
| Solubilizer (Symrise) | PEG-40 Hydrogenated Castor Oil, Trideceth-9, Propylene Glycol, Water (Aqua) | — | — | — | — | — | 2.0 | — | — |
| Symdiol 68 (Symrise) | 1,2 Hexanediol, Caprylylglycol | — | — | — | — | 1.0 | — | — | — |
| Symrise fragrance | Fragrance | 0.3 | 0.3 | 0.3 | 0.2 | 0.4 | 0.2 | 0.5 | — |
| Texapon N 70 (Cognis) | Sodium Laureth Sulfate | — | 10.0 | — | — | — | — | — | — |
| Water, demineralized | Water (Aqua) | Ad 100 | Ad 100 | Ad 100 | Ad 100 | Ad 100 | Ad 100 | Ad 100 | Ad 100 |

Particularly preferred areas of application for the mixtures according to the invention are cosmetic products for treating itchy, dry skin, in particular an itchy, dry scalp, including especially antidandruff shampoos and other hair and scalp care products, such as all conceivable types of shampoo (including shampoos for normal hair, greasy hair and dry, coarse (damaged) hair, 2-in-1 shampoo, baby shampoo, shampoo for dry scalp, shampoo concentrate), conditioners, hair treatments, hair lotions, hair rinses, hair creams, pomades, perming and setting agents, hair smoothing agents (straightening agents, relaxers), hair sprays, styling aids (e.g. gels or waxes); bleaching agents, hair colorants, e.g. temporary, direct hair colorants, semipermanent hair colorants, permanent hair colorants; perming preparations and perming-setting agents; and pharmaceutical agents for combating diseases/scalp damage associated with itching.

Specific Embodiments

In specific embodiment one, the invention is a mixture comprising or consisting of:
(a) one or more compounds of Formula 1:

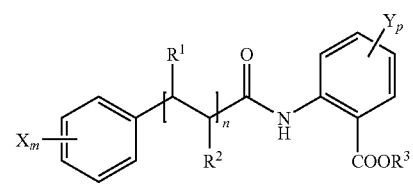

where the symbols in the compound or each compound of Formula 1 are defined as follows:
m=0, 1, 2 or 3,
p=0, 1 or 2,
n=0, 1 or 2,
where, when n=1 or 2, $R^1$ and $R^2$ in pairs are each H or together are another chemical bond;
where, when m=1, 2 or 3, each X independently of the others is OH, Oalkyl or Oacyl,
and where, when p=1 or 2, each Y independently of the others is OH, Oalkyl or Oacyl,
and
$R^3$=H or alkyl, $R^3$=H also representing the corresponding cosmetically or pharmaceutically acceptable salts and solvates,
and
(b) one or more antidandruff agents.

In specific embodiment two the invention is a mixture as in specific embodiment one, wherein the antidandruff agent(s) is (are) present in an amount that synergistically intensifies the itch-alleviating action of the substance(s) of Formula 1.

In specific embodiment three, the invention is a mixture as in specific embodiments 1 or 2 wherein the following definitions apply to the compound of Formula 1:
n=1 or 2 and the sum p+m>0
and/or
p+m>0 and X or Y is selected at least once from the group comprising OH and Oacyl.

In specific embodiment four, the invention is a mixture as in specific embodiment three wherein the following definitions apply to the compound of Formula 1:
n=1
and
p+m 2,
with the proviso that X and Y together are selected at least twice from the group comprising OH and Oacyl.

In specific embodiment five, the invention is a mixture as in specific embodiments one or two wherein the following definitions apply to the compound of Formula 1:
n=1,
and also:
m=1, 2 or 3, with the proviso that X is selected at least once from the group comprising OH and Oacyl,
and/or
p=1 or 2,
with the proviso that Y is selected at least once from the group comprising OH and Oacyl.

In specific embodiment six the invention is a mixture as in one of the preceding specific embodiments wherein the following definitions apply to the compound of Formula 1:
n=1
and
$R^1$ and $R^2$ are each H or together are another chemical bond.

In specific embodiment seven, the invention is a mixture as in specific embodiment three wherein the compound of Formula 1 is selected from the group comprising:

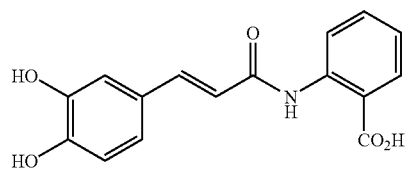

2

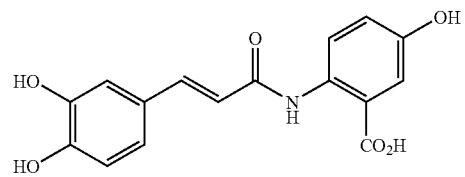

3

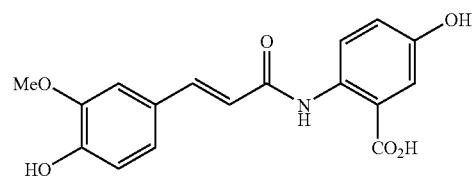

4

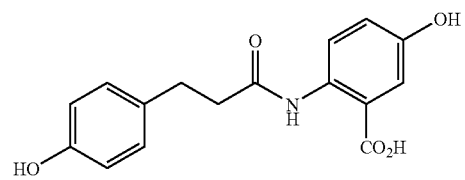

5

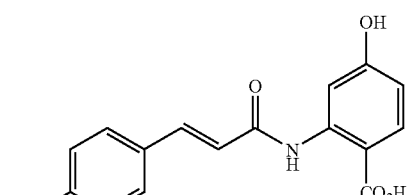

6

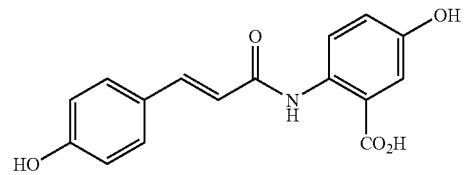

7

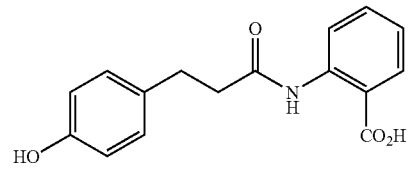

8

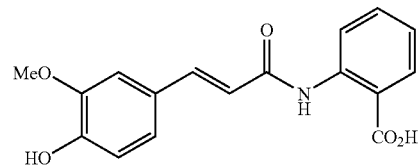

9

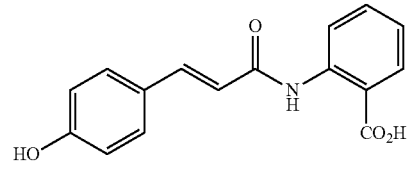

10

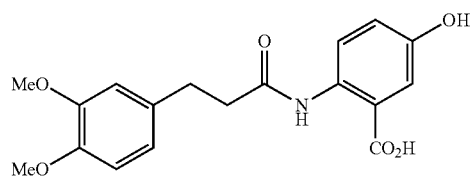
11
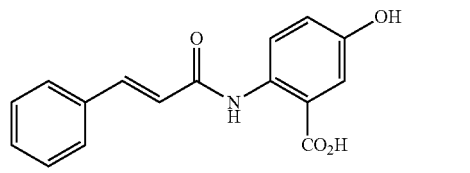
12
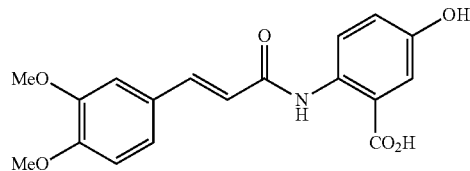
13
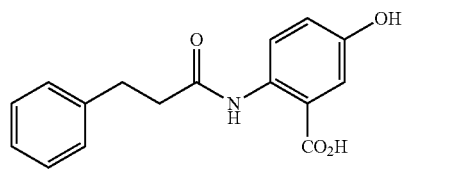
30
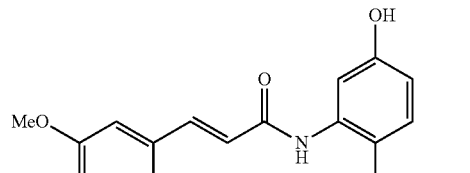
31
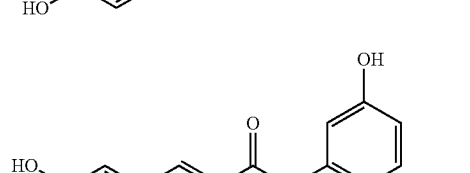
32
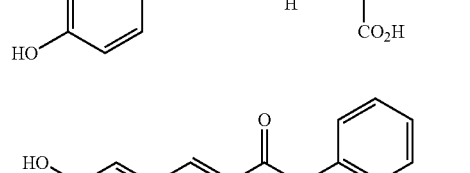
33
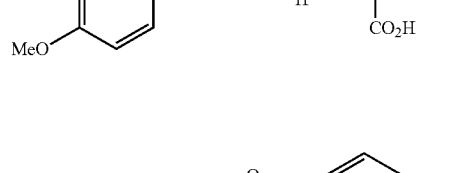
36
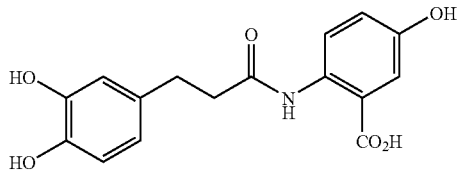
37
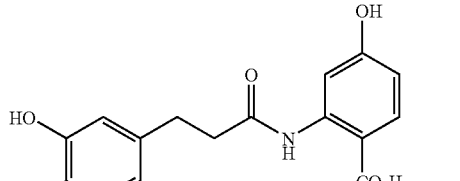
38
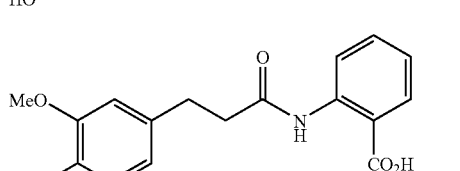
39
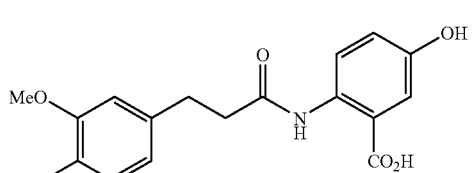
40
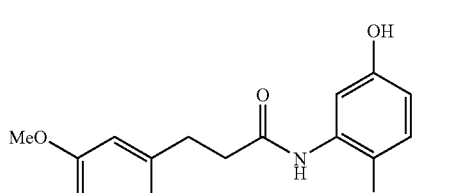
41
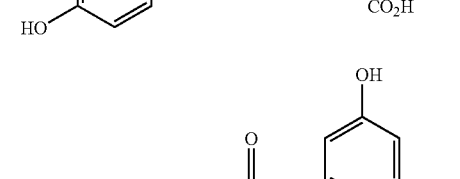
42
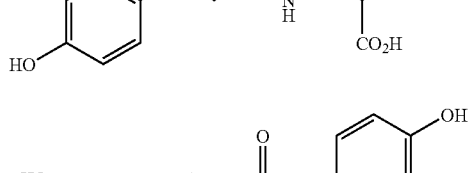
43
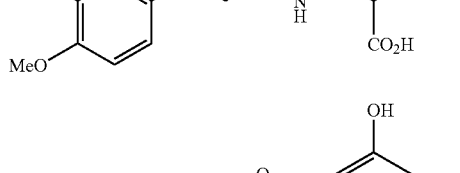
44

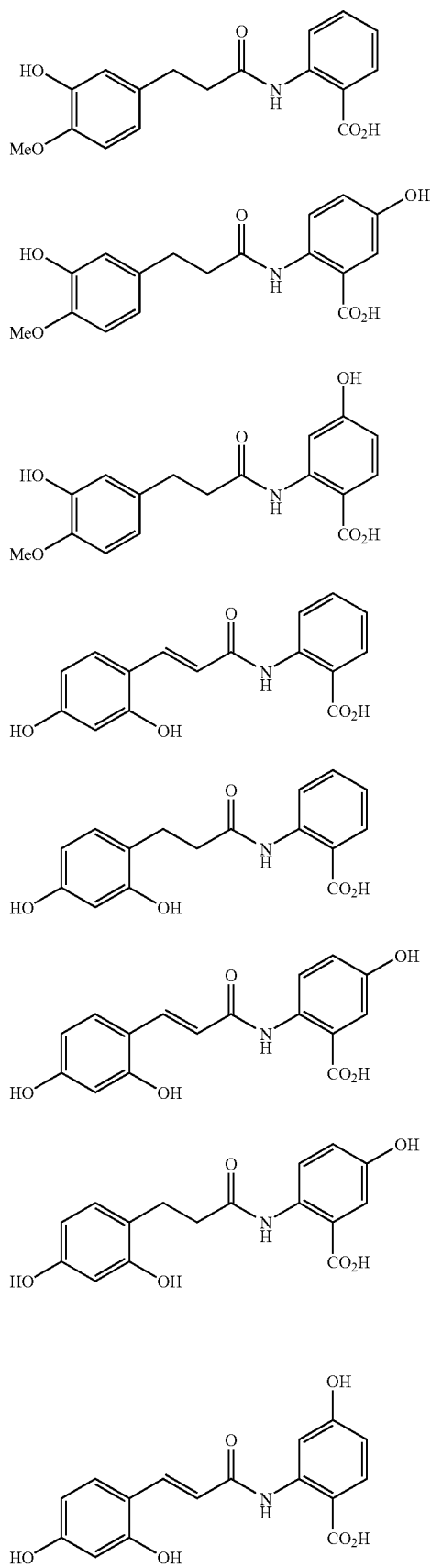
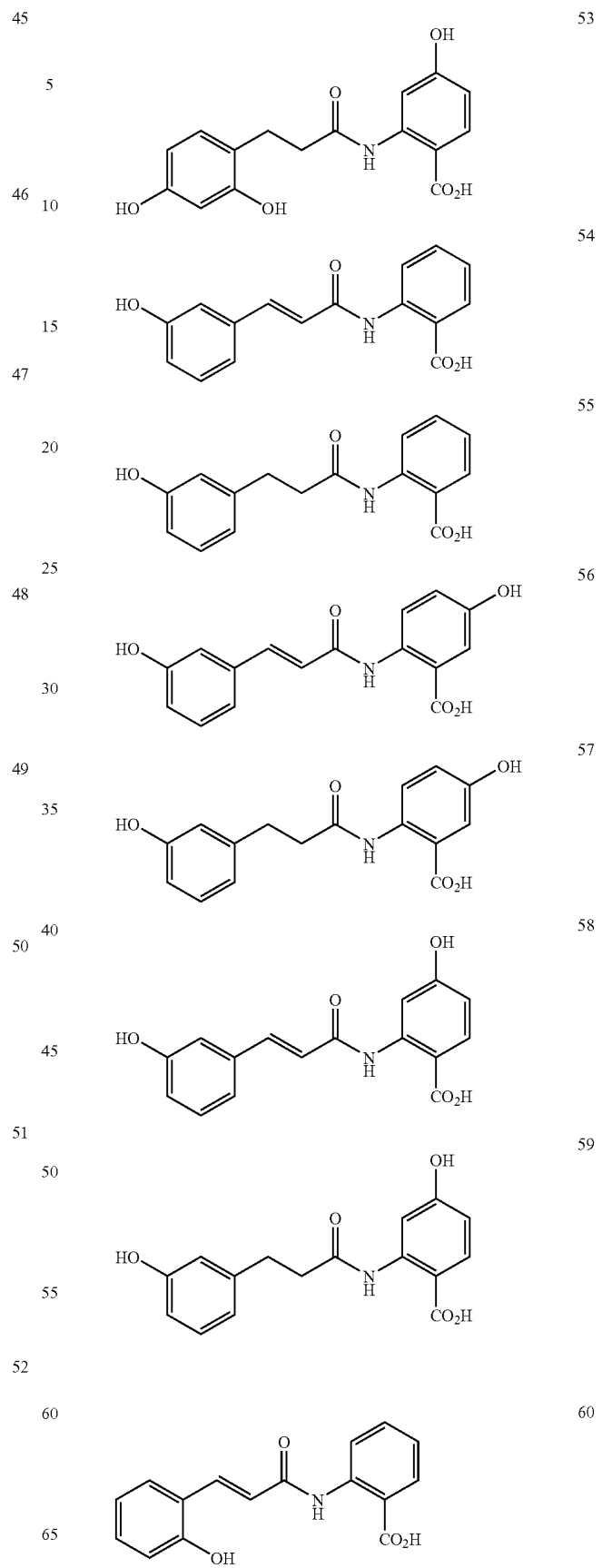

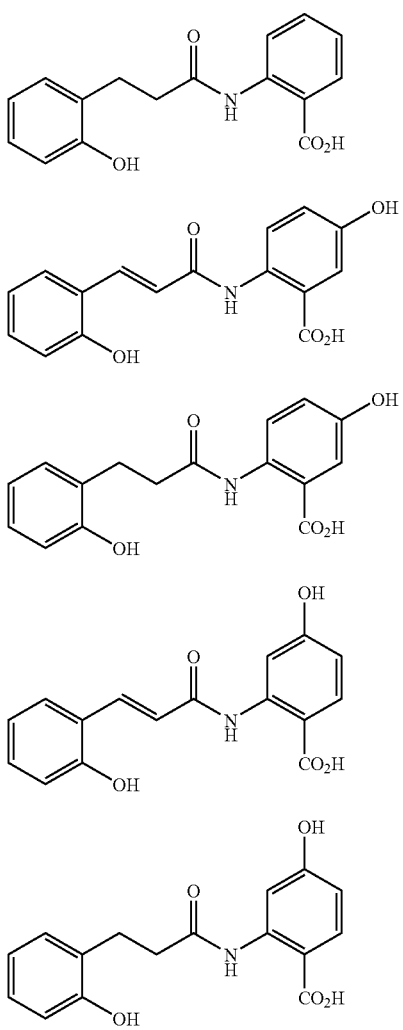

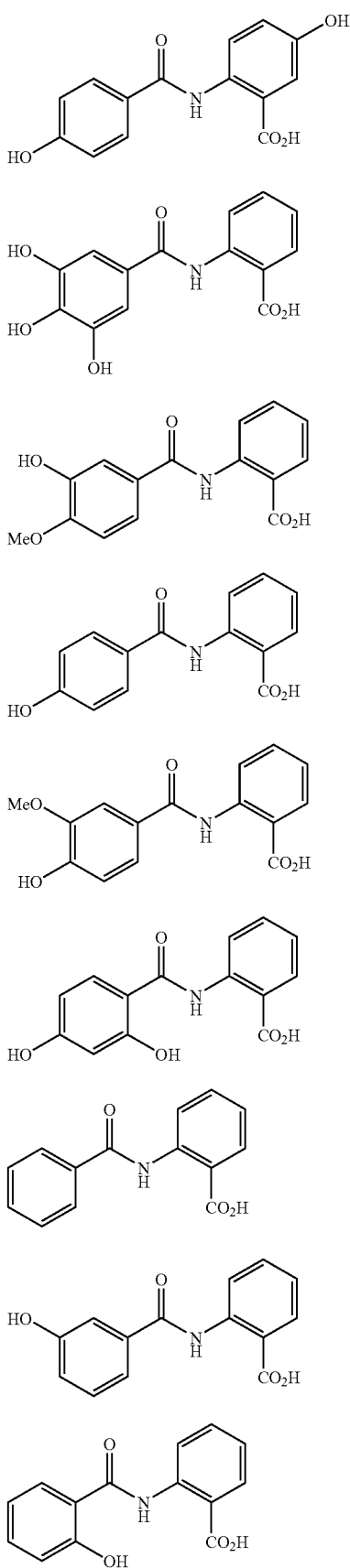

In specific embodiment eight, the invention is a mixture as in specific embodiment one or two wherein the following definition applies to the compound of Formula 1:

n=0.

In specific embodiment nine, the invention is a mixture as in specific embodiment eight wherein the following definition applies to the compound of Formula 1:

m+p 2, with the proviso that at least two of the substituents X and Y are selected from the group comprising OH and Oacyl.

In specific embodiment ten, the invention is a mixture as in specific embodiments eight or nine wherein the compound of Formula 1 is selected from the group comprising:

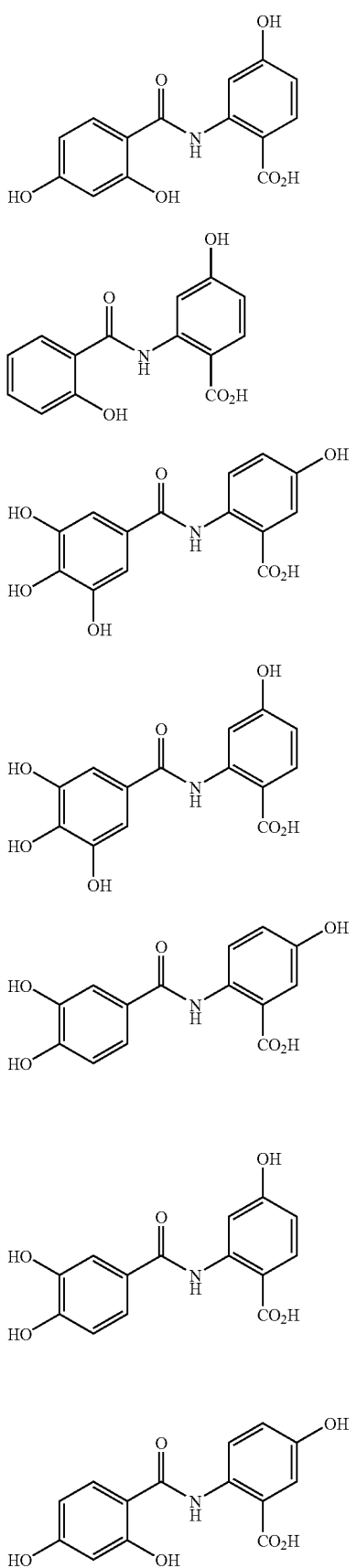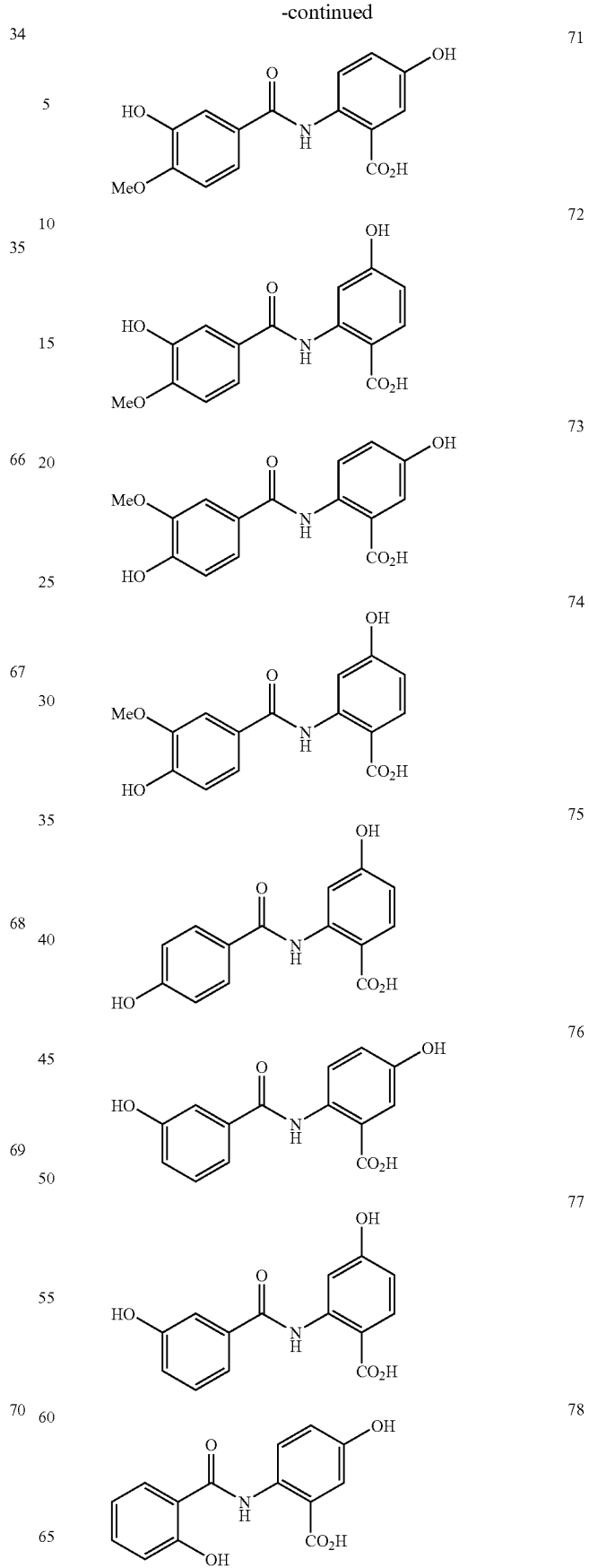

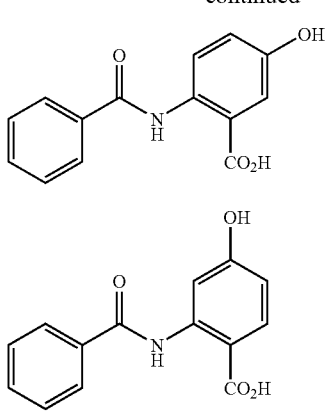

79

80

In specific embodiment eleven, the invention is a mixture as in specific embodiment one or two wherein the following definition applies:

$R^3$=$CH_3$ or linear or branched alkyl having 2 to 30 C atoms.

In specific embodiment twelve, the invention is a mixture as claimed in one of the preceding specific embodiments wherein the antidandruff agent(s) is (are) selected from the group comprising:

one or more azoles, including climbazole, benzimidazole, benzothiazole, bifonazole, butaconazole nitrate, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, thioconazole, diazoles and triazoles, e.g. terconazole and itraconazole, one or more pyrithione salts, including the sodium, zinc, tin, calcium, magnesium, aluminum and zirconium salts of 1-hydroxy-2-pyrithione, coal tar, sulfur, selenium sulfides, aluminum chloride, octopirox (INCI: Piroctone Olamine), cyclopiroxolamines, undecylenic acid and its metal salts, potassium permanganate, sodium thiosulfate, propylene glycol, other branched and unbranched aliphatic diols and polyols (especially 1,2-diols having 5-18 carbon atoms), urea preparations, griseofulvin, 8-hydroxyquinoline, ciloquinol, thiobendazole, thiocarbamates, triclosan, haloprogin, polyenes, hydroxypyridone, morpholine, benzylamine, allylamines (especially terbinafine), tea tree oil, clove oil, coriander oil, palmarosa oil, thyme oil and cinnamon oil, as well as ethereal oil of bitter orange, cinnamaldehyde, citronellic acid, farnesol, berberine, hinokitiol, tropolone, birch tar oils, ichthyol (sulfonated shale oil), Sensiva SC-50 (ethylhexyl glycerol), polyglycerol esters, e.g. polyglycerol-3 caprylate, arylalkyl alcohols, e.g. phenylethyl alcohol, 3-phenyl-1-propanol, vetikol (4-methyl-4-phenyl-2-pentanol), muguet alcohol (2,2-dimethyl-3-phenylpropanol), Elestab HP-100, azelaic acid, lyticase, isothiazalinones, especially octylisothiazalinone, and iodopropynyl butyl carbamate (IPBC).

In specific embodiment thirteen, the invention is a mixture as in one of the preceding specific embodiments wherein the amount of compound(s) of Formula 1 and/or the amount of antidandruff agent(s), each taken by itself, has no action in the alleviation of itching or the reduction of skin reddening, but the total amount of compound(s) of Formula 1 and antidandruff agent(s) does have such an action.

In specific embodiment fourteen, the invention is mixtures as in one of the preceding specific embodiments wherein the weight ratio of the total amount of compounds of Formula 1 to the total amount of antidandruff agents ranges from 1:100 to 2:1.

In specific embodiment fifteen, the invention is mixtures as in one of the preceding specific embodiments wherein the antidandruff agent(s) is (are) selected from the group comprising climbazole and other azoles, pyrithione salts, especially zinc pyrithione, ichthyol and octopirox, and mixtures of these substances.

In specific embodiment sixteen, the invention is mixtures as in one of the preceding specific embodiments which also include a cooling agent from the group comprising l-menthol, d-menthol, racemic menthol, menthone glycerol acetal, menthyl lactate (especially l-menthyl lactate and l-menthyl l-lactate), substituted menthyl-3-carboxamides, 2-isopropyl-N-2,3-trimethylbutanamide, substituted cyclohexanecarboxamides, 3-menthoxypropane-1,2-diol, 2-hydroxyethyl menthyl carbonate, 2-hydroxypropyl menthyl carbonate, N-acetylglycine menthyl ester, isopulegol, hydroxycarboxylic acid menthyl esters (e.g. menthyl 3-hydroxybutyrate), monomenthyl succinate, 2-mercaptocyclodecanone, menthyl 2-pyrrolidin-5-onecarboxylate, 2,3-dihydroxy-p-menthane, 3,3,5-trimethylcyclohexanone glycerol ketal, 3-menthyl-3,6-di- and trioxaalkanoates, 3-menthyl methoxyacetate and icilin, and mixtures of these substances.

In specific embodiment seventeen, the invention is use of a mixture as in one of the preceding specific embodiments as a cosmetic composition for the treatment or prevention of itching (pruritus) and/or for the reduction of skin reddening or for the preparation of a drug for the treatment or prevention of itching (pruritus) and/or for the reduction of skin reddening.

In specific embodiment eighteen, the invention is a method of alleviating itching and/or reducing skin reddening, comprising the following step:

application to the skin of a mixture as in one of specific embodiments one to sixteen in an amount that alleviates itching and/or reduces skin reddening.

In specific embodiment nineteen, the invention is use of an antidandruff agent for the synergistic intensification of the action of a compound of Formula 1:

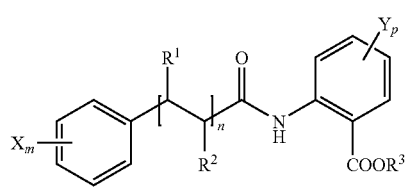

1 in the alleviation of itching or the reduction of skin reddening, wherein the following definitions apply to the compound of Formula 1:

m=0, 1, 2 or 3, p=0, 1 or 2, n=0, 1 or 2, where, when n=1 or 2, $R^1$ and $R^2$ in pairs are each H or together are another chemical bond, where, when m=1, 2 or 3, each X independently of the others is OH, Oalkyl or Oacyl, and where, when p=1 or 2, each Y independently of the others is OH, Oalkyl or Oacyl, and
R³═H or alkyl, R³═H also representing the corresponding cosmetically or pharmaceutically acceptable salts and solvates.

What is claimed is:

1. A composition comprising:
   (a) dihydroavenanthramide D
   and
   (b) climbazole,
   wherein the climbazole is present in the amount of 0.01 to 20 wt %, and
   wherein dihydroavenanthramide D is present in the amount of 0.001 to 1 wt. %, based on the total weight of the composition.

2. The composition as claimed in claim 1, wherein the weight ratio of the total amount of the dihydroavenanthramide D to the amount of climbazole ranges from 1:100 to 2:1.

3. The composition as claimed in claim 1, further comprising a cooling agent selected from the group consisting of l-menthol, d-menthol, racemic menthol, menthone glycerol acetal, menthyl lactate, l-menthyl lactate, l-menthyl l-lactate, substituted menthyl-3-carboxamides, 2-isopropyl-N-2,3-trimethylbutanamide, substituted cyclohexanecarboxamides, 3-menthoxypropane-1,2-diol, 2-hydroxyethyl menthyl carbonate, 2-hydroxypropyl menthyl carbonate, N-acetylglycine menthyl ester, isopulegol, hydroxycarboxylic acid menthyl esters, menthyl 3-hydroxybutyrate, monomenthyl succinate, 2-mercaptocyclodecanone, menthyl 2-pyrrolidin-5-onecarboxylate, 2,3-dihydroxy-p-menthane, 3,3,5-trimethylcyclohexanone glycerol ketal, 3-menthyl-3,6-di- and tioxaalkanoates, 3-menthyl methoxyacetate and icilin, and mixtures thereof.

4. A method for treating itching (puritus) comprising applying a composition as claimed in claim 1 to skin and/or hair.

5. A method for reducing skin reddening, comprising applying a composition as claimed in claim 1 to skin.

6. A cosmetic or pharmaceutical end product, comprising a composition as claimed in claim 1 and at least one carrier or excipient.

7. The composition of claim 1, wherein dihydroavenanthramide D is present in the amount of 0.001 to 0.2 wt. %, based on the total weight of the composition.

8. The composition of claim 2, wherein the weight ratio of the total amount of the dihydroavenanthramide D to the amount of climbazole ranges from 1:10 to 1:2.

9. The composition of claim 3, wherein the cooling agent is present in the amount of 0.01 to 20 wt. %, based on the total weight of the composition.

10. The composition of claim 3, wherein the cooling agent is present in the amount of 0.1 to 5 wt. %, based on the total weight of the composition.

11. The composition of claim 1, further comprising one or more other components selected from the group consisting of skin moisture regulators, osmolytes, keratolytic substances, preservatives, antiperspirants, solvents anti-inflammatory compounds, antioxidants, vitamins, skin tighteners, skin tanning agents, plant extracts, and surfactants.

12. The position of claim 1, wherein the composition is in the form of an emulsion.

13. The composition of claim 11 wherein the one or more other components are selected from the group consisting of chelators and animal and/or vegetable hydrolyzates.

* * * * *